(12) United States Patent
Reiche et al.

(10) Patent No.: US 10,688,116 B2
(45) Date of Patent: *Jun. 23, 2020

(54) TREATMENT OF METABOLIC DISORDERS IN EQUINE ANIMALS

(71) Applicant: Boehringer Ingelheim Vetmedica GmbH, Ingelheim am Rhein (DE)

(72) Inventors: Dania Birte Reiche, Bingen am Rhein (DE); Nicole Mohren, Jugenheim (DE); Laura Johnston, Thornleigh (AU); Bruce Somerville, Parkville, MO (US); Rebecca K. Voth, Smithville, MO (US)

(*) Notice: Subject to any disclaimer, the term of this patent is extended or adjusted under 35 U.S.C. 154(b) by 103 days.

This patent is subject to a terminal disclaimer.

(21) Appl. No.: 14/672,705

(22) Filed: Mar. 30, 2015

(65) Prior Publication Data
US 2015/0272977 A1    Oct. 1, 2015

(30) Foreign Application Priority Data

Apr. 1, 2014  (EP) .................................. 14162983
Jul. 11, 2014  (EP) .................................. 14176714
Oct. 1, 2014  (EP) .................................. 14187223

(51) Int. Cl.
| | | |
|---|---|---|
| A61P 5/50 | (2006.01) | |
| C07D 309/10 | (2006.01) | |
| A61P 3/10 | (2006.01) | |
| A61K 31/351 | (2006.01) | |
| A61K 31/7034 | (2006.01) | |
| A61K 31/7042 | (2006.01) | |
| A61K 31/7048 | (2006.01) | |
| A61K 31/7056 | (2006.01) | |
| A61K 47/02 | (2006.01) | |
| A61K 9/20 | (2006.01) | |
| A61K 9/48 | (2006.01) | |
| A61K 9/02 | (2006.01) | |
| A61K 9/08 | (2006.01) | |
| A61K 31/382 | (2006.01) | |

(52) U.S. Cl.
CPC ............ *A61K 31/7034* (2013.01); *A61K 9/02* (2013.01); *A61K 9/08* (2013.01); *A61K 9/2059* (2013.01); *A61K 9/4866* (2013.01); *A61K 31/351* (2013.01); *A61K 31/382* (2013.01); *A61K 31/7042* (2013.01); *A61K 31/7048* (2013.01); *A61K 31/7056* (2013.01); *A61K 47/02* (2013.01); *A61P 3/10* (2018.01); *A61P 5/50* (2018.01); *C07D 309/10* (2013.01)

(58) Field of Classification Search
None
See application file for complete search history.

(56) References Cited

U.S. PATENT DOCUMENTS

| | | | |
|---|---|---|---|
| 7,371,732 B2 | 5/2008 | Eickelmann et al. | |
| 7,375,090 B2 | 5/2008 | Himmelsbach et al. | |
| 7,393,836 B2 | 7/2008 | Eckhardt et al. | |
| 7,417,032 B2 | 8/2008 | Eckhardt et al. | |
| 7,419,959 B2 | 9/2008 | Eckhardt et al. | |
| 7,524,822 B2 | 4/2009 | Kraemer et al. | |
| 7,579,449 B2 | 8/2009 | Eckhardt et al. | |
| 7,589,193 B2 | 9/2009 | Washburn et al. | |
| 7,683,160 B2 | 3/2010 | Eckhardt et al. | |
| 7,687,469 B2 | 3/2010 | Eckhardt et al. | |
| 7,713,938 B2 | 5/2010 | Himmelsbach et al. | |
| 7,723,309 B2 | 5/2010 | Himmelsbach et al. | |
| 7,745,414 B2 | 6/2010 | Eckhardt et al. | |
| 7,772,191 B2 | 8/2010 | Eckhardt et al. | |
| 7,772,378 B2 | 8/2010 | Himmelsbach et al. | |
| 7,776,830 B2 | 8/2010 | Eckhardt et al. | |
| 7,847,074 B2 | 12/2010 | Eckhardt et al. | |
| 7,851,502 B2 | 12/2010 | Bindra et al. | |
| 7,851,602 B2 | 12/2010 | Himmelsbach et al. | |
| 7,858,587 B2 | 12/2010 | Eckhardt et al. | |
| 7,879,806 B2 | 2/2011 | Himmelsbach et al. | |
| 7,879,807 B2 | 2/2011 | Himmelsbach et al. | |
| 8,039,441 B2 | 10/2011 | Himmelsbach et al. | |
| 8,080,580 B2 * | 12/2011 | Mascitti ............... | C07D 493/08 514/456 |
| 8,283,326 B2 | 10/2012 | Eckhardt et al. | |
| 8,283,454 B2 | 10/2012 | Liou et al. | |
| 8,507,450 B2 | 8/2013 | Eckhardt et al. | |
| 8,551,957 B2 | 10/2013 | Dugi et al. | |
| 8,987,323 B2 * | 3/2015 | Cai ....................... | C07D 309/10 514/183 |
| 9,145,434 B2 | 9/2015 | Eckhardt et al. | |
| 10,220,017 B2 * | 3/2019 | Weiler ................ | A61K 31/351 |
| 2003/0064935 A1 | 4/2003 | Gougoutas | |
| 2007/0259821 A1 | 11/2007 | Eckhardt et al. | |
| 2009/0143316 A1 | 6/2009 | Imamura et al. | |

(Continued)

FOREIGN PATENT DOCUMENTS

| | | |
|---|---|---|
| CA | 2519584 A1 | 9/2004 |
| EP | 2048150 A1 | 4/2009 |

(Continued)

OTHER PUBLICATIONS

French et al., "Pharmacokinetics and metabolic effects of triamcinolone acetonide and their possible relationships to glucocorticoid-induced laminitis in horses" J. Vet. Pharmacol. Therap. vol. 23 pp. 287-292 (Year: 2000).*

(Continued)

*Primary Examiner* — Eric Olson
(74) *Attorney, Agent, or Firm* — John Ezcurra

(57) ABSTRACT

The present invention relates to one or more SGLT2 inhibitors or pharmaceutically acceptable forms thereof for use in the treatment and/or prevention of a metabolic disorder of an equine animal. In particular, the present invention relates to one or more SGLT2 inhibitors or a pharmaceutically acceptable form thereof for use in the treatment and/or prevention of laminitis, vascular dysfunction, hypertension, hepatic lipidosis, atherosclerosis, hyperadrenocorticism, Pituitary Pars Intermedia Dysfunction and/or Equine Metabolic Syndrome in an equine animal.

16 Claims, 13 Drawing Sheets

(56) References Cited

U.S. PATENT DOCUMENTS

| | | | |
|---|---|---|---|
| 2010/0167988 A1* | 7/2010 | Gant | C07B 59/002 514/1.1 |
| 2010/0167989 A1 | 7/2010 | Gant | |
| 2010/0249392 A1 | 9/2010 | Eckhardt et al. | |
| 2012/0237593 A1 | 9/2012 | Comiskey et al. | |
| 2012/0277175 A1 | 11/2012 | Neto et al. | |
| 2014/0031540 A1* | 1/2014 | Eckhardt | C07H 15/26 536/55 |
| 2014/0303096 A1 | 10/2014 | Reiche et al. | |
| 2015/0164856 A1 | 6/2015 | Reiche et al. | |
| 2016/0361289 A1 | 12/2016 | Kley et al. | |
| 2017/0056366 A1 | 3/2017 | Weiler et al. | |
| 2017/0071969 A1* | 3/2017 | Reiche | C07H 15/207 |
| 2017/0239281 A1* | 8/2017 | Reiche | A61K 31/4045 |

FOREIGN PATENT DOCUMENTS

| | | | |
|---|---|---|---|
| EP | 2368552 A1 | 9/2011 | |
| WO | 0127128 A1 | 4/2001 | |
| WO | 2002083066 A2 | 10/2002 | |
| WO | 2004063209 A2 | 7/2004 | |
| WO | 2007077457 A2 | 7/2007 | |
| WO | 2007093610 A1 | 8/2007 | |
| WO | WO2007/093610 * | 8/2007 | C07D 309/10 |
| WO | 2007128749 A1 | 11/2007 | |
| WO | 2007129053 A1 | 11/2007 | |
| WO | 2008002824 A1 | 1/2008 | |
| WO | 2008042688 A2 | 4/2008 | |
| WO | 2008116179 A1 | 9/2008 | |
| WO | 2009124755 A1 | 10/2009 | |
| WO | 2009143020 A1 | 11/2009 | |
| WO | 2010022313 A2 | 2/2010 | |
| WO | 2010023594 A1 | 3/2010 | |
| WO | 2010048358 A2 | 4/2010 | |
| WO | 2010092125 A1 | 8/2010 | |
| WO | 2010092123 A8 | 6/2011 | |
| WO | 2011117295 A1 | 9/2011 | |
| WO | 2011153712 A1 | 12/2011 | |
| WO | 2012062698 A1 | 5/2012 | |
| WO | 2012140597 A1 | 10/2012 | |
| WO | 2013040164 A1 | 3/2013 | |
| WO | 2013040165 A1 | 3/2013 | |
| WO | 2014016381 A1 | 1/2014 | |
| WO | 2014068007 A1 | 5/2014 | |
| WO | 2014161836 A1 | 10/2014 | |
| WO | 2015091313 A1 | 6/2015 | |
| WO | 2015110402 A1 | 7/2015 | |
| WO | 2015150299 A2 | 10/2015 | |
| WO | 2016046150 A1 | 3/2016 | |
| WO | 2017032799 A1 | 3/2017 | |

OTHER PUBLICATIONS

Treiber et al., "Laminitis in Ponise is a Diabetic-like State" Experimental Biology 2007: Meeting abstracts p. A833, No. 737.23 (Year: 2007).*

Johnson et al., "Medical Implications of Obesity in Horses—Lessons for Human Obesity" Journa lof Diabetes Science and Technology vol. 3 issue 1, pp. 163-174 (Year: 2009).*

Frank et al., "Equine Metabolic Syndrome", ACVIM Consensus Statement, Journal of Veterinary Internal Medicine, vol. 24, No. 3, 2010, pp. 467-475.

Gehlen et al., "Comparison of Insulin and Glucose Metabolism in Horses with Pituitary Pars Intermedia Dysfunction Treated Versus Not Treated with Pergolide". Journal of Equine Veterinary Science, vol. 34, 2014, pp. 508-513.

Hirayama et al., Common mechanisms of inhibition for the Na+/glucose (hSGLT1) and Na+/C1-GABA (HGAT1) contransporters). British Journal of Pharmacology, vol. 134, Oct. 2001, pp. 484-495.

International Search Report and Written Opinion for PCT/EP2015/056840 dated Nov. 9, 2015.

Kakinuma et al., "(1S)-1-,5-Anhydro-1-[5-(4-ethoxybenzyl)-2-methoxy-4-methylphenyl]-1-thio-d-glucitol (TS-071) is a Potent, Selective Sodium-Dependent Glucose Cotransporter 2 (SGLT2) Inhibitor for Type 2 Diabetes Treatment" Journal of Medicinal Chemistry, vol. 53, No. 8, 2010, pp. 3247-3261.

Tirmenstein et al., "Nonclinical Toxicology Assessments Support the Chronic Safety of Dapagliflozin, a First-in-Class Sodium-Glucose Cotransporter 2 Inhibitor". International Journal of Toxicology, vol. 32, No. 5, 2013, pp. 336-350.

Xu et al., "Design, Synthesis, and Biological Evaluation of Deuterated C-Aryl Glycoside as a Potent and Long-Acting Renal Sodium-Dependent Glucose Cotransporter 2 Inhibitor for the Treatment of Type 2 Diabetes". Journal of Medicinal Chemistry, vol. 57, 2014, pp. 1236-1251.

De Laat et al., "Equine laminitis: Induced by 48 h hyperinsulinaemia in Standardbred horses". Equine Veterinary Journal, vol. 42, No. 2, 2010, pp. 129-135.

Deshpande et al., "A Practival Stereoselective Synthesis and Novel Cocrystallizations of an Amphiphatic SGLT-2 Inhibitor". Organic Process Research & Development, vol. 16, 2012, pp. 577-585.

Ciobotaru, Emilia, "Diabetes Mellitus—Insights and Perspectives", Editor: Oluwafemi O. Oguntibeju, ISBN 978-953-51-0939-6, Jan. 2, 2013, Chapter 15, Spontaneous Diabetes Mellitus in Animals, pp. 271-296.

Yamamoto et al., "TS-071 is a novel, potent and selective renal sodium-glucose cotransporter 2 (SGLT2) inhibitor with anti-hyperglycaemic activity." British Journal of Pharmacology, vol. 164, No. 1, 2011, pp. 181-191.

Katsuno et al., "Sergliflozin, a Novel Selective Inhibitor of Low-Affinity Sodium Glucose Cotransporter (SGLT2), Validates the Critical Role of SGLT2 in Renal Glucose Reabsorption and Modulates Plasma Glucose Level." The Journal of Pharmacology and Experimental Therapeutics, vol. 320, No. 1, 2007, pp. 323-330.

Ueta et al., "Reduction of Renal Transport Maximum for Glucose by Inhibition of Na+-Glucose Cotransporter Suppresses Blood Glucose Elevation in Dogs." Biological and Pharmaceutical Bulletin, vol. 29, No. 1, 2006, pp. 114-118.

Grempler et al., "Empagliflozin, a novel selective sodium glucose cotransporter-2 (SGLT-2) inhibitor: characterisation and comparison with other SGLT-2 inhibitors." Diabetes, Obesity and Metabolism, vol. 14, 2012, pp. 83-90.

Sugimoto et al., "Novel Therapeutic Agents for the Treatment of Diabetes Sodium-Glucose Co-Transporter (SGLT) 2 Inhibitors." Cutting-Edge of Medicine, vol. 102, No. 6, 2013, pp. 1474-1483.

Diabetes, vol. 56, Suppl.1, 2007, pp. A144-A145.

Sinha et al., "Pioglitazone—Do we really need it to manage type 2 diabetes?", Diabetes & Metabolic Syndrome: Clinical Research & Reviews, 7 (2013) pp. 52-55.

Durham et al., "Type 2 diabetes mellitus with pancreatic B cell dysfunction in 3 horses confirmed with minimal model analysis", Equine Beterninary Journal (2009) 41 (9), pp. 924-929.

Suga et al., "SGLT1 in pancreatic a cells regulates glucagon secretion in mice, possible explaining the distinct effects STGLT2 inhibitors on plasma glucagon levels", Molecular Metabolism 19 (2018), 12 pages.

* cited by examiner

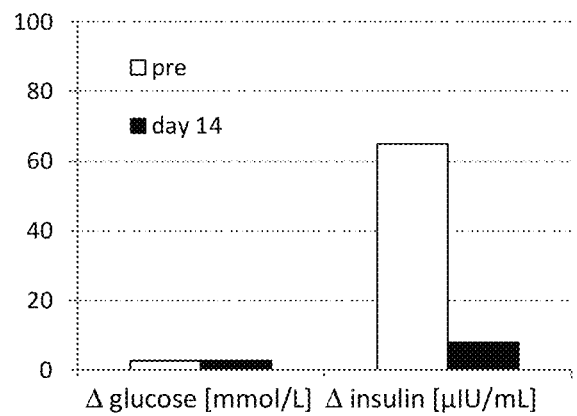
FIG. 15A - horse treated with compound A
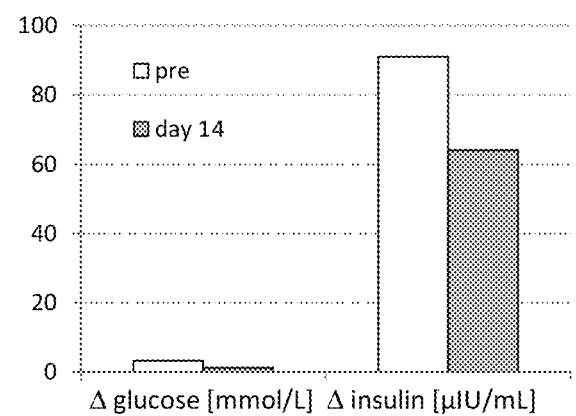
FIG. 15B - horse receiving placebo

TREATMENT OF METABOLIC DISORDERS IN EQUINE ANIMALS

FIELD OF THE INVENTION

The present invention relates to veterinary medicine, in particular to the treatment and/or prevention of metabolic disorders in equine animals.

BACKGROUND OF THE INVENTION

Equine animals, e.g., horses, are affected by various metabolic disorders, including insulin resistance and hyperinsulinaemia. Such insulin-related disorders in equine animals, for example, are only rarely associated with diabetes mellitus and hyperglycemia, as it is in humans or various other mammals. However, in equine animals, insulin also regulates vital metabolic functions; e.g., insulin drives glucose into tissues such as liver, adipose, and skeletal muscle; induces vasoconstrictive and vasodilatory pathways; and regulates protein and fat metabolism. Insulin-related disorders thus have a severe and life-threatening impact on the health of equine animals. They are correlated or may be associated with a number of further equine disorders, conditions or syndromes, including impaired glucose tolerance, dyslipidemia, dysadipokinemia, obesity and/or regional adiposity, subclinical inflammation or systemic inflammation, in particular low grade systemic inflammation, which also comprises adipose tissue, Equine Metabolic Syndrome (EMS) and/or Equine Pituitary Pars Intermedia Dysfunction (PPID), also known as equine Cushing's syndrome, which are characterized e.g. by laminitis, vascular dysfunction, hypertension, hepatic lipidosis, hyperadrenocorticism and/or atherosclerosis.

In particular, insulin resistance in equine animals may be associated with EMS and/or PPID or may cause the development or progression of PPID. EMS and/or PPID may become manifest e.g., in laminitis. This devastating worldwide cause of mortality in horses is a multifactorial condition causing structural and mechanical changes in the supporting tissues within the hoof, resulting in acute and chronic pain, lameness, and potentially euthanasia. Equine laminae are highly metabolically active, and a complex microvascular bed is present. A significant body of evidence exists also for vascular dysfunction (endothelial cell dysfunction) during equine laminitis (ref. 1: Katz & Bailey, 2012). In vitro studies in equine digital vessels have shown insulin resistance mediated endothelial and/or vascular dysfunction (ref. 2: Venugopal et al., 2011). A direct link between hyperinsulinaemia and laminitis has been documented in naturally-occurring forms of the disease (ref. 3: Treiber et al., 2006). However, the mechanism by which insulin resistance and/or hyperinsulinemia cause EMS and/or PPID, in particular vascular dysfunction and/or laminitis in horses is poorly understood.

No satisfactory treatment is currently available for metabolic disorders such as insulin resistance, hyperinsulinaemia and associated disorders in equine animals, such as EMS and/or in case they are associated with or secondary to e.g., PPID, which become manifested e.g., by laminitis, vascular dysfunction, hypertension in equine animals. For instance, the use of Metformin is controversially discussed (ref. 4: Tinworth et al., 2012). Similarly, treatment of equine PPID with pergolide seems to hardly affect insulin resistance and/or hyperinsulinemia (ref. 5: Gehlen, 2014).

In human medicine, insulin resistance, e.g., when manifested as diabetes mellitus type 2, is a well-recognized condition, and may lead in particular to hyperglycemia (pathologically increased plasma glucose levels). Several oral antihyperglycemic drugs are approved for human diabetes. These drugs act, e.g., by stimulating pancreatic insulin secretion in a glucose-independent or glucose-dependent manner (sulfonylurea/meglitinides, or DPP IV inhibitors, respectively), by enhancing tissue sensitivity to insulin (biguanides, thiazolidinediones), or by slowing postprandial intestinal glucose absorption (alpha-glucosidase inhibitors).

Other antihyperglycemic approaches have been contemplated for treating diabetes and high blood sugar, including inhibition of the renal sodium-dependent glucose cotransporter SGLT2. SGLT2 in the kidney regulates glucose levels by mediating the reabsorption of glucose back into the plasma following filtration of the blood. SGLT2 inhibition thus induces glucosuria or glycosuria and may reduce blood glucose levels.

SGLT2 inhibition has not previously been contemplated for use in equine animals, in particular in insulin-resistant equine animals. In equine animals, insulin-resistance, i.e., failure of tissues to respond appropriately to insulin, generally becomes manifested as hyperinsulinemia. When insulin-resistant target tissues, e.g., skeletal muscle, have a reduced capacity for glucose uptake, the pancreas is stimulated to release more insulin, leading to hyperinsulinaemia. However, unlike in humans, e.g., insulin resistance in equine animals, e.g., horses, is generally not associated with hyperglycemia (ref. 6: Frank et al., 2011). Insulin-resistant equine animals, e.g., horses, do not appear to have high blood glucose. For that reason, it would appear to be counterintuitive to apply an approach that reduces blood glucose by transferring glucose out of the blood into the urine, even if this was previously known in a context of high blood glucose.

DISCLOSURE OF THE INVENTION

Summary of the Invention

The present invention has surprisingly found that inhibition of SGLT2 is effective and safe in the treatment and/or prevention of metabolic disorders in equine animals. The present invention thus provides the use of one or more SGLT2 inhibitors or pharmaceutically acceptable forms thereof in the treatment and/or prevention of a metabolic disorder of an equine animal. Further aspects of the invention are defined below, as well as in the claims.

According to the invention, the metabolic disorder may be insulin resistance, hyperinsulinemia, and/or a clinical condition/sign associated with insulin resistance and/or hyperinsulinemia.

The metabolic disorder, or said clinical condition/sign associated with insulin resistance and/or hyperinsulinemia, may be one or more disorder selected from insulin resistance, hyperinsulinemia, impaired glucose tolerance, dyslipidemia, dysadipokinemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction and/or Equine Metabolic Syndrome.

According to the invention, the equine animal may be suffering from one or more of impaired glucose tolerance, dyslipidemia, dysadipokinemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction and/or Equine Metabolic Syndrome.

According to the invention, impaired glucose tolerance, dyslipidemia, dysadipokinemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction and/or Equine Metabolic Syndrome may be associated with hyperinsulinemia and/or insulin resistance.

According to the invention, the metabolic disorder may be hyperinsulinemia and/or insulin resistance, and said hyperinsulinemia or insulin resistance may optionally be associated with one or more of impaired glucose tolerance, dyslipidemia, dysadipokinemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction and/or Equine Metabolic Syndrome.

The equine animal may, e.g., be a horse. The equine animal may, e.g., be a pony. The equine animal may be obese and/or exhibit regional adiposity. However, for instance as regards Pituitary Pars Intermedia Dysfunction, the equine animal may also be not obese and/or be present with muscle wasting and/or exhibit hyperglycemia.

The pharmaceutically acceptable form of the one or more SGLT2 inhibitors may be a crystalline complex between the one or more SGLT2 inhibitors and one or more amino acids, e.g., proline.

According to the invention, the one or more SGLT2 inhibitors or pharmaceutically acceptable forms thereof may be provided, e.g., for oral or parenteral administration, preferably for oral administration.

The one or more SGLT2 inhibitors or pharmaceutically acceptable forms thereof may be administered in dosages of 0.01 to 3.0 mg/kg body weight per day, preferably from 0.02 to 1.0 mg/kg body weight per day, more preferably from 0.03 to 0.4 mg/kg body weight per day. Thus, the one or more SGLT2 inhibitors or pharmaceutically acceptable forms thereof may be prepared for the administration of 0.01 to 3.0 mg/kg body weight per day, preferably from 0.02 to 1.0 mg/kg body weight per day, more preferably from 0.03 to 0.4 mg/kg body weight per day.

The one or more SGLT2 inhibitors or pharmaceutically acceptable forms thereof is preferably administered only once per day.

According to the present invention, any SGLT2 inhibitor or pharmaceutically acceptable form thereof may be used. In preferred embodiments, the one or more SGLT2 inhibitors are a glucopyranosyl-substituted benzene derivative. A number of SGLT2 inhibitors which may be used according to the invention are described in detail below.

The present invention also provides a pharmaceutical composition comprising one or more SGLT2 inhibitors or a pharmaceutically acceptable form thereof, for use according to the invention as disclosed herein.

In the examples provided herein, therapeutic and prophylactic benefits resulting from inhibition of SGLT2 according to the present invention are demonstrated experimentally. Experimental data disclosed herein are intended to illustrate the invention, but not to have any limiting effect upon the scope of protection, which is defined herein below by the claims.

In particular, the present invention has surprisingly found that the use of one or more SGLT2 inhibitors according to the present invention advantageously leads to a reduction in insulin resistance in treated, insulin resistant equine animals. That is, equivalently, the use of one or more SGLT2 inhibitors according to the present invention advantageously leads to increased insulin sensitivity in treated, insulin resistant equine animals.

The use of one or more SGLT2 inhibitors according to the present invention advantageously leads to reduced plasma insulin levels, i.e., allows effective treatment of hyperinsulinemia. Thus, the use of one or more SGLT2 inhibitors according to the present invention advantageously leads to reduced baseline plasma insulin levels, and/or a reduced insulin excursion due to a glycemic challenge, e.g., as measured during an intravenous glucose tolerance test (ivGTT), an oral sugar test (OST) or after any other form of glucose intake, e.g., after a meal (postprandial insulin excursion).

The use of one or more SGLT2 inhibitors according to the present invention advantageously leads to a reduction in hyperinsulinemia and surrogate markers of insulin resistance in treated, insulin resistant equine animals.

The glucose excursion after a challenge with insulin (e.g., in an intravenous insulin tolerance test (ivITT)), or after a challenge with glucose (e.g., as measured during an intravenous glucose tolerance test (ivGTT), an oral sugar test (OST) or after any other form of glucose intake, e.g., after a meal (postprandial glucose excursion)), or as measured in a combined glucose-insulin tolerance test (CGIT), of an equine animal treated in accordance with the invention is, advantageously, also improved. That is, after a challenge with insulin, the decrease in glucose levels is greater and/or more rapid; or after a challenge with glucose, the glycemic peak of the glucose excursion is lowered and/or the duration of the glucose excursion is reduced.

The use of one or more SGLT2 inhibitors according to the present invention thus generally leads to improved (i.e., increased) glucose tolerance, i.e., equivalently, reduces glucose intolerance.

The use of one or more SGLT2 inhibitors according to the present invention advantageously also leads to a reduction in plasma levels of non-esterified fatty acids, or an improved elimination of non-esterified fatty acids (NEFAs) from the bloodstream e.g., after a challenge with insulin (e.g., as measured during an intravenous insulin tolerance test (ivITT)), or after a challenge with glucose (e.g., as measured during an intravenous glucose tolerance test (ivGTT), an oral sugar test (OST) or after any other form of glucose intake, e.g., after a meal, that initiates a blood insulin excursion, or as measured in a combined glucose-insulin tolerance test (CGIT).

The use of one or more SGLT2 inhibitors according to the present invention advantageously also leads to a reduction in body fat and improved adipokine profile, e.g., reduced blood leptin levels. The invention is also associated with anti-obesity effects, and/or lead to a decrease in body mass in an equine animal. In one aspect, the invention thus allows obesity and/or obesity-related metabolic disorders to be managed in an equine animal.

The use of one or more SGLT2 inhibitors according to the present invention generally reduces dyslipidemia, dysadipokinemia, obesity and/or regional adiposity. Thus, the use of SGLT2 inhibitors allows for the treatment and/or prevention of dyslipidemia, dysadipokinemia, obesity and/or regional adiposity, in particular when associated with insulin resistance and/or hyperinsulinemia in equine animal.

Advantageously, the use of one or more SGLT2 inhibitors according to the present invention does not cause hypoglycemia.

The effects of the uses according to the present invention (i.e., the above-mentioned beneficial effects upon insulin resistance/sensitivity, insulin excursion, second phase insulin secretion, glucose tolerance, elimination of non-esterified fatty acids, body fat, and/or blood leptin levels) are also advantageous in that they allow for the prevention of complications of insulin resistance and/or hyperinsulinemia, and the treatment, prevention or control of further metabolic disorders, symptoms and/or clinical conditions/signs/signs that are associated with insulin resistance and/or hyperinsulinemia in equine animals. They thus allow the possibility of preventing and/or delaying the onset of such complications, further metabolic disorders, symptoms and/or clinical condition/signs in equine animals.

The use of one or more SGLT2 inhibitors according to the present invention also provides for treatment and/or prevention of laminitis, i.e., leads to reduction of lameness and/or time to recovery from a laminitis episode.

The use of one or more SGLT2 inhibitors according to the present invention provides for treatment and/or prevention of vascular dysfunction, i.e., improvement of altered digital perfusion and/or improved vascular response to contractile or dilatatory stimuli.

The use of one or more SGLT2 inhibitors according to the present invention also provides for treatment and/or prevention of Equine Metabolic Syndrome (EMS).

The use of one or more SGLT2 inhibitors according to the present invention also provides for treatment and/or prevention of Pituitary Pars Intermedia Dysfunction (PPID), for instance prevention of the development and/or progression of Pituitary Pars Intermedia Dysfunction (PPID) in an equine animal. That is the onset and/or progression of Pituitary Pars Intermedia Dysfunction (PPID) in an equine animal may be fully inhibited or delayed.

The use of one or more SGLT2 inhibitors according to the present invention may prevent the development and/or recurrence of laminitis in an equine animal suffering from EMS and/or PPID.

The use of one or more SGLT2 inhibitors according to the present invention may prevent the development and/or recurrence of vascular dysfunction in an equine animal suffering from EMS and/or PPID.

The use of one or more SGLT2 inhibitors according to the present invention may prevent the development and/or recurrence of hypertension in an equine animal suffering from EMS and/or PPID.

The use of one or more SGLT2 inhibitors according to the present invention may prevent the development and/or recurrence of hepatic lipidosis in an equine animal suffering from EMS and/or PPID.

The use of one or more SGLT2 inhibitors according to the present invention may prevent the development and/or recurrence of regional obesitas in an equine animal suffering from EMS and/or PPID.

A further advantage of the present invention is that the use of SGLT2 inhibitors is effective against the metabolic disorders alone, i.e., if desired the use of one or more SGLT2 inhibitors in an equine animal provides a monotherapy (i.e. a stand-alone therapy; i.e., no other medication is administered to the equine animal for the treatment or prevention of the same metabolic disorder). The invention also allows for the possibility for combination therapy with another drug (e.g., a further insulin sensitizing drug).

The effects of using one or more SGLT2 inhibitors according to the present invention (e.g., the above-mentioned beneficial effects upon insulin resistance/sensitivity, plasma insulin levels, insulin excursion, glucose excursion, glucose tolerance, elimination of non-esterified fatty acids, body fat, and/or blood leptin levels) may be relative to the same or a comparable equine animal prior to administration of one or more SGLT2 inhibitors according to the present invention, and/or relative to a comparable equine animal that has not received said treatment (e.g., a placebo group). In either case, when a comparison is made, the comparison may be made after a certain treatment period, e.g., 0.5, 1, 2, 3 or 4 months. Preferably the treatment period is 3 or more months.

A further advantage of the present invention is that one or more SGLT2 inhibitors may effectively be administered to an equine animal orally, e.g., in liquid form. Moreover, SGLT2 inhibitors according to the present invention can be administered only once per day. These advantages allow for optimal dosing and compliance of the treated equine animal.

Generally, the use of SGLT2 inhibitors according to the present invention may thus attenuate, delay or prevent the progression of a metabolic disorder, e.g., the metabolic disorders disclosed herein, or may delay or prevent the onset of metabolic disorders and their complications in equine animals.

The invention also provides methods of treating or preventing metabolic disorders in equine animals, comprising administering to an equine animal in need of such treatment or prevention an effective dose of one or more SGLT2 inhibitors as described herein.

In a preferred embodiment, the present invention thus provides the use of one or more SGLT2 inhibitors or pharmaceutically acceptable forms thereof in the treatment and/or prevention of recurrent laminitis associated with hyperinsulinemia in equine animals, preferably horses, with insulin resistance.

In another preferred embodiment, the present invention thus provides the use of one or more SGLT2 inhibitors or pharmaceutically acceptable forms thereof in the treatment and/or prevention of recurrent laminitis associated with Equine Metabolic Syndrome (EMS) in equine animals, preferably horses.

In yet another preferred embodiment, the present invention thus provides the use of one or more SGLT2 inhibitors or pharmaceutically acceptable forms thereof in the treatment and/or prevention of the clinical conditions/signs associated with Equine Metabolic Syndrome (EMS) or Equine Metabolic Syndrome (EMS) in equine animals, preferably horses, wherein preferably said clinical conditions/signs may be one or more disorder selected from insulin resistance, hyperinsulinemia, impaired glucose tolerance, dyslipidemia, dysadipokinemia, subclinical inflammation, systemic inflammation, low grade systemic inflammation, which also comprises adipose tissue, obesity, regional adiposity, laminitis, vascular dysfunction, hypertension, hepatic lipidosis, atherosclerosis, hyperadrenocorticism, Pituitary Pars Intermedia Dysfunction and/or Equine Metabolic Syndrome.

Definitions

All values and concentrations presented herein are subject to inherent variations acceptable in biological science within an error off 10%. The term "about" also refers to this acceptable variation.

Treatment effects disclosed herein (such as an improvement, reduction or delayed onset of a disorder, disease or condition, or the improvement, reduction, increase or delay of any effect, index, marker level or other parameter relating to a disorder, disease or condition) may be observed with a statistical significance of $p<0.05$, preferably $<0.01$.

When reference is made herein to a deviation (e.g., an increase, elevation, excess, prolongation, raise, reduction, decrease, improvement, delay, abnormal levels, or any other change, alteration or deviation with respect to a reference), the deviation may be, e.g., by 5% or more, particularly 10% or more, more particularly 15% or more, more particularly 20% or more, more particularly 30% or more, more particularly 40% or more, or more particularly 50% or more, with respect to the relevant reference value, unless otherwise stated. Typically, the deviation will be by at least 10%, i.e., 10% or more. The deviation may also be by 20%. The deviation may also be by 30%. The deviation may also be by 40%. The relevant reference value may be generated from a group of reference animals which are treated with placebo instead of an SGLT2 inhibitor.

Herein, an excursion, e.g., an insulin excursions or glucose excursion, designates a change in concentration or level in blood over time. The magnitude of excursions, e.g., insulin excursions or glucose excursions may be expressed as area-under-curve (AUC) values.

Herein, the terms "active substance" or "active ingredient" encompass one or more SGLT2 inhibitors or any pharmaceutically acceptable form thereof (e.g., a prodrug or a crystalline form), for use according to the invention. In the case of a combination with one or additional active compound, the terms "active ingredient" or "active substance" may also include the additional active compound.

Herein, the expression "associated with", in particular encompasses the expression "caused by".

Herein, ivGTT refers to an intravenous glucose tolerance test. In an ivGTT, 0.2 g dextrose per kg body mass may typically be employed.

Herein, ivITT refers to an intravenous insulin tolerance test. In an ivITT, 0.03 U insulin per kg body mass may typically be employed.

Herein, CGIT refers to a combined glucose-insulin tolerance test. In a CGIT, 0.15 mg glucose per kg body mass and 0.1 U insulin per kg body mass may typically be employed.

Herein, OST refers to an oral sugar test. In an OST, 0.15 mL corn syrup per kg body mass may typically be employed.

SGLT2 Inhibitors

SGLT2 inhibitors for use according to the invention include, but are not limited to, glucopyranosyl-substituted benzene derivatives, for example as described in WO01/27128 (ref. 7), WO03/099836 (ref. 8), WO2005/092877 (ref. 9), WO2006/034489 (ref. 10), WO2006/064033 (ref. 11), WO2006/117359 (ref. 12), WO2006/117360 (ref. 13), WO2007/025943 (ref. 14), WO2007/028814 (ref. 15), WO2007/031548 (ref. 16), WO2007/093610 (ref. 17), WO2007/128749 (ref. 18), WO2008/049923 (ref. 19), WO2008/055870 (ref. 20), WO2008/055940 (ref. 21), WO2009/022020 (ref. 22) or WO2009/022008 (ref. 23), all hereby incorporated by reference.

Moreover, a SGLT2 inhibitor for use according to the invention may be selected from the group consisting of the following compounds or pharmaceutically acceptable forms thereof:

(1) a glucopyranosyl-substituted benzene derivative of the formula (1)

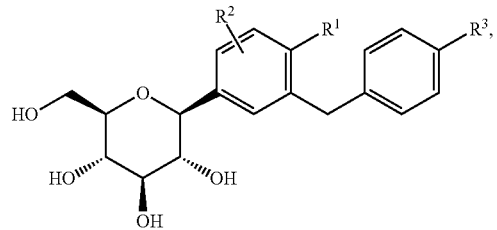

wherein $R^1$ denotes cyano, Cl or methyl (most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein R3 is preferably selected from cyclopropyl, ethyl, ethinyl, ethoxy, (R)-tetrahydrofuran-3-yloxy or (S)-tetrahydrofuran-3-yloxy; and most preferably R3 is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenyl carbonyl and phenyl-($C_{1-3}$-alkyl)-carbonyl;

(2) 1-cyano-2-(4-cyclopropyl-benzyl)-4-(β-D-glucopyranos-1-yl)-benzene, represented by formula (2):

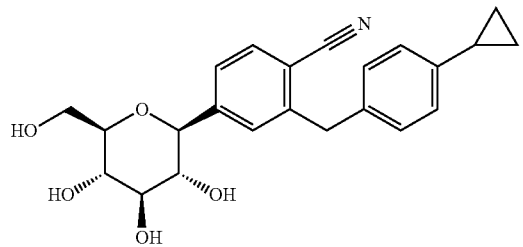 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

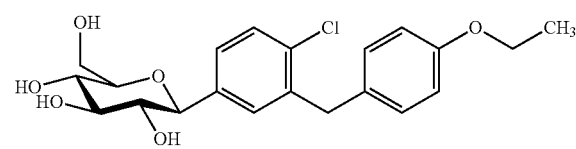

(4) Canagliflozin, represented by formula (4):
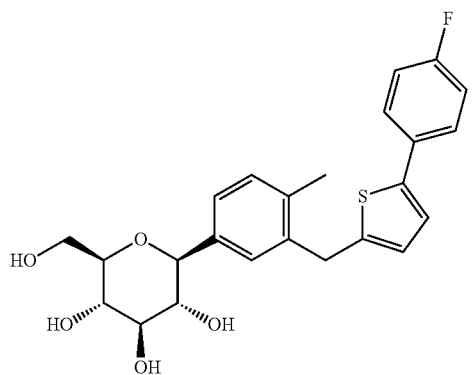 [SMILES: Cc1ccc([C@@H]2O[C@H](CO)[C@@H](O)[C@H](O)[C@H]2O)cc1Cc1ccc(-c2ccc(F)cc2)s1]
(5) Empagliflozin, represented by formula (5):
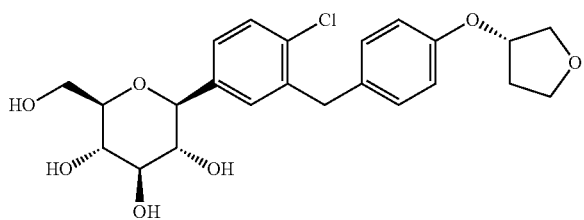 [SMILES: OC[C@H]1O[C@@H](c2ccc(Cl)c(Cc3ccc(O[C@H]4CCOC4)cc3)c2)[C@H](O)[C@@H](O)[C@@H]1O]
(6) Luseogliflozin, represented by formula (6):
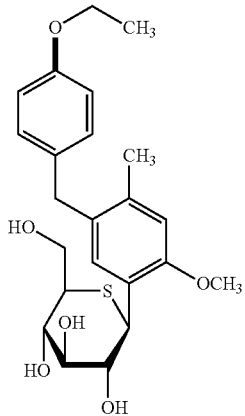
(7) Tofogliflozin, represented by formula (7):
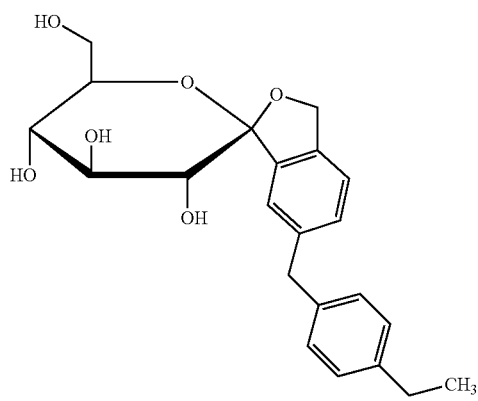
(8) Ipragliflozin, represented by formula (8):
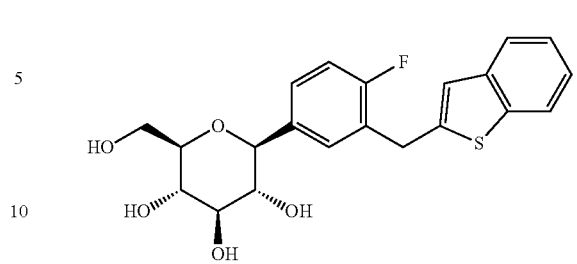
(9) Ertugliflozin, represented by formula (9):
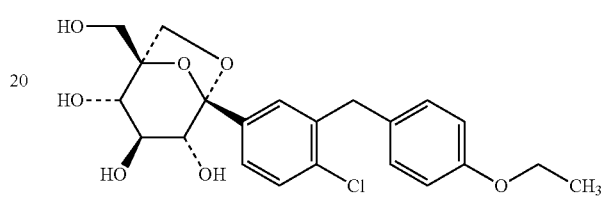
(10) Atigliflozin, represented by formula (10):
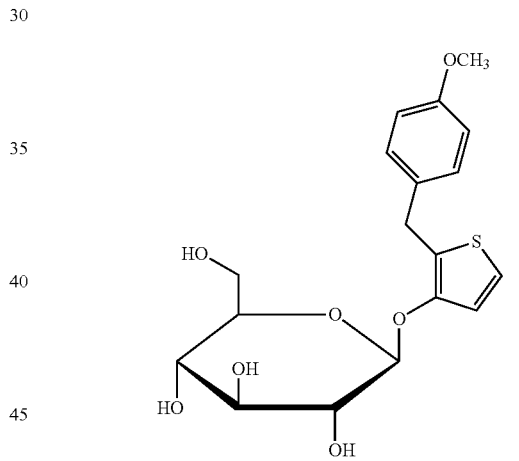
(11) Remogliflozin, represented by formula (11):
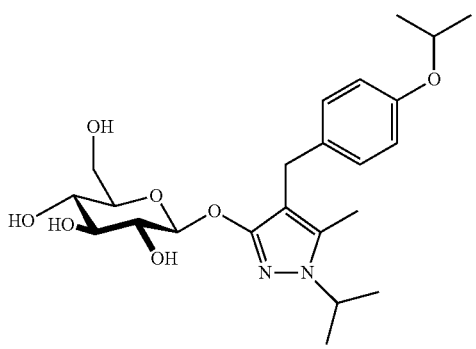

(12) a thiophene derivative of the formula (12)

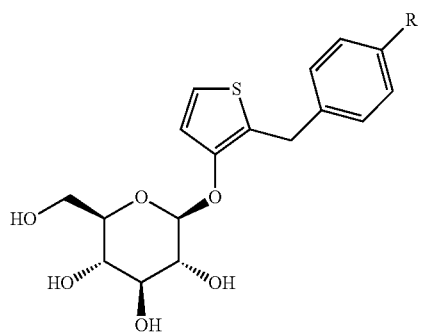

(7-1)

wherein R denotes methoxy or trifluoromethoxy;

(13) 1-(β-D-glucopyranosyl)-4-methyl-3-[5-(4-fluorophenyl)-2-thienylmethyl]benzene as described in WO2005/012326, represented by formula (13);

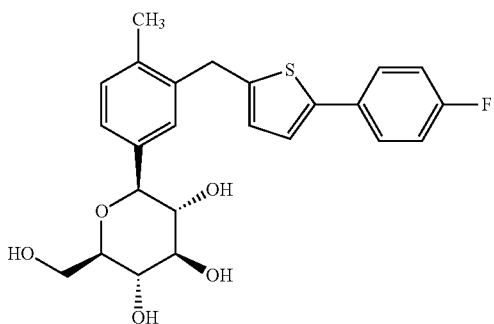 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

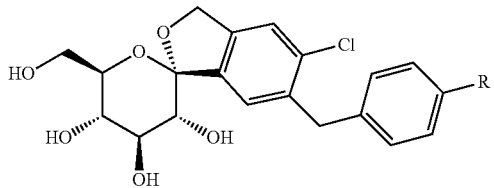

wherein R denotes methoxy, trifluoromethoxy, ethoxy, ethyl, isopropyl or tert. butyl;

(15) a pyrazole-O-glucoside derivative of the formula (15)

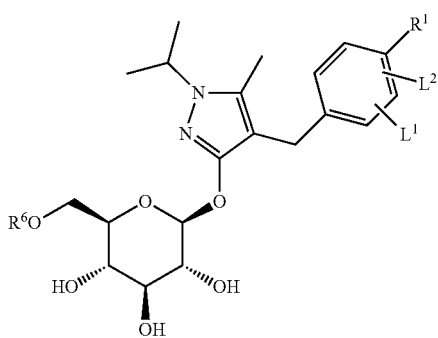

wherein
R¹ denotes $C_{1-3}$-alkoxy,
L¹, L² independently of each other denote H or F,
R⁶ denotes H, ($C_{1-3}$-alkyl)carbonyl, ($C_{1-6}$-alkyl)oxycarbonyl, phenyloxycarbonyl, benzyloxycarbonyl or benzylcarbonyl;

(16) a compound of the formula (16):

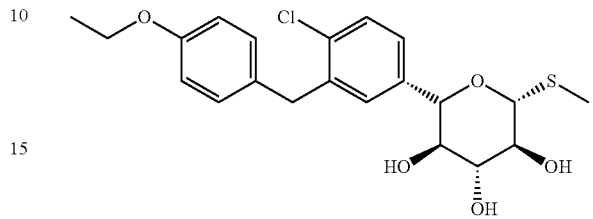

(17) and Sergliflozin, represented by formula (17):

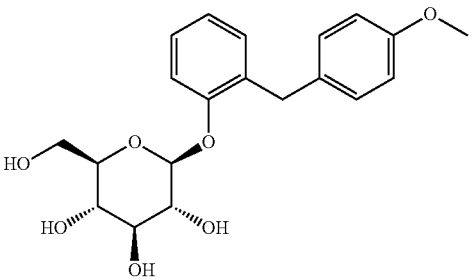 [SMILES: COc1ccc(Cc2ccccc2O[C@@H]2O[C@H](CO)[C@@H](O)[C@H](O)[C@H]2O)cc1]

The term "dapagliflozin" as employed herein refers to dapagliflozin of the above structure as well as pharmaceutically acceptable forms thereof, including hydrates and solvates thereof, and crystalline forms thereof. The compound and methods of its synthesis are described in WO03/099836 (ref. 8) for example. Preferred hydrates, solvates and crystalline forms are described in the patent applications WO2008/116179 (ref. 24) and WO2008/002824 (ref. 25) for example.

The term "canagliflozin" as employed herein refers to canagliflozin of the above structure as well as pharmaceutically acceptable forms thereof, including hydrates and solvates thereof, and crystalline forms thereof. The compound and methods of its synthesis are described in WO2005/012326 (ref. 26) and WO2009/035969 (ref. 27) for example. Preferred hydrates, solvates and crystalline forms are described in the patent application WO2008/069327 (ref. 28) for example.

The term "empagliflozin" as employed herein refers to empagliflozin of the above structure as well as pharmaceutically acceptable forms thereof, including hydrates and solvates thereof, and crystalline forms thereof. The compound and methods of its synthesis are described in WO2005/092877 (ref. 9), WO2006/120208 (ref. 29) and WO2011/039108 (ref. 30) for example. A preferred crystalline form is described in the patent applications WO2006/117359 (ref. 12) and WO2011/039107 (ref. 31) for example.

The term "atigliflozin" as employed herein refers to atigliflozin of the above structure as well as pharmaceutically acceptable forms thereof, including hydrates and solvates thereof, and crystalline forms thereof. The compound and methods of its synthesis are described in WO2004/007517 (ref. 32) for example.

The term "ipragliflozin" as employed herein refers to ipragliflozin of the above structure as well as pharmaceutically acceptable forms thereof, including hydrates and solvates thereof, and crystalline forms thereof. The compound and methods of its synthesis are described in WO2004/080990 (ref. 33), WO2005/012326 (ref. 26) and WO2007/114475 (ref. 34) for example.

The term "tofogliflozin" as employed herein refers to tofogliflozin of the above structure as well as pharmaceutically acceptable forms thereof, including hydrates and solvates thereof, and crystalline forms thereof. The compound and methods of its synthesis are described in WO2007/140191 (ref. 35) and WO2008/013280 (ref. 36) for example.

The term "luseogliflozin" as employed herein refers to luseogliflozin of the above structure as well as pharmaceutically acceptable forms thereof, including hydrates and solvates thereof, and crystalline forms thereof.

The term "ertugliflozin" as employed herein refers to ertugliflozin of the above structure as well as pharmaceutically acceptable forms thereof, including hydrates and solvates thereof, and crystalline forms thereof. The compound is described for example in WO2010/023594 (ref. 37).

The term "remogliflozin" as employed herein refers to remogliflozin of the above structure as well as pharmaceutically acceptable forms thereof, including prodrugs of remogliflozin, in particular remogliflozin etabonate, including hydrates and solvates thereof, and crystalline forms thereof. Methods of its synthesis are described in the patent applications EP1213296 (ref. 38) and EP1354888 (ref. 39) for example.

The term "sergliflozin" as employed herein refers to sergliflozin of the above structure as well as pharmaceutically acceptable forms thereof, including prodrugs of sergliflozin, in particular sergliflozin etabonate, including hydrates and solvates thereof, and crystalline forms thereof. Methods for its manufacture are described in the patent applications EP1344780 (ref. 40) and EP1489089 (ref. 41) for example.

The compound of formula (16) above and its manufacture are described for example in WO2008/042688 (ref. 42) or WO2009/014970 (ref. 43).

Preferred SGLT2 inhibitors are glucopyranosyl-substituted benzene derivatives. Optionally, one or more hydroxyl groups of the glucopyranosyl group in such one or more SGLT2 inhibitors may be acylated with groups selected from ($C_{1-18}$-alkyl)carbonyl, ($C_{1-18}$-alkyl)oxycarbonyl, phenyl carbonyl and phenyl-($C_{1-3}$-alkyl)-carbonyl.

More preferred are glucopyranosyl-substituted benzonitrile derivatives of formula (1) as disclosed herein above. Yet more preferred are glucopyranosyl-substituted benzonitrile derivatives of formula (18):

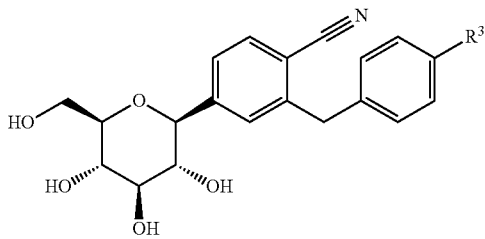

wherein R3 denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methy 1-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano (wherein R3 is preferably selected from cyclopropyl, ethyl, ethinyl, ethoxy, (R)-tetrahydrofuran-3-yloxy or (S)-tetrahydrofuran-3-yloxy; and R3 most preferably is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenyl carbonyl and phenyl-($C_{1-3}$-alkyl)-carbonyl.

Preferably, such SGLT2 inhibitor is 1-cyano-2-(4-cyclopropyl-benzyl)-4-(β-D-glucopyranos-1-yl)-benzene as shown in formula (2) (also referred to herein as "compound A"). Optionally, one or more hydroxyl groups of the β-D-glucopyranosyl group of compound A may be acylated with groups selected from ($C_{1-18}$-alkyl)carbonyl, ($C_{1-18}$-alkyl)oxycarbonyl, phenyl carbonyl and phenyl-($C_{1-3}$-alkyl)-carbonyl.

Thus, in preferred embodiments, a SGLT2 inhibitor according to the present invention is a glucopyranosyl-substituted benzene derivative SGLT2 inhibitor, preferably a SGLT2 inhibitor of formula (1), more preferably of formula (18), or yet more preferably of formula (2) (i.e., compound A), in each case as defined herein above.

Metabolic Disorders

According to the invention, metabolic disorders or metabolic diseases are all kinds of disturbances of the energy metabolism, affecting e.g., the turnover of carbohydrates and/or of fat. It is preferred to affect the control of the energy metabolism, especially the glucose metabolism by influencing the responsible regulatory network, e.g., via modulation of the activity and/or concentrations of insulin.

The metabolic disorder may be an insulin-related disorder. In particular, the metabolic disorder may be insulin resistance (or, equivalently, impaired insulin sensitivity). Insulin resistance may be associated with a further metabolic disorder or clinical condition/sign, e.g., insulin resistance may be associated with impaired glucose tolerance, dyslipidemia, dysadipokinemia, subclinical inflammation, systemic inflammation, low grade systemic inflammation, which also comprises adipose tissue, obesity and/or regional adiposity. Additionally or alternatively, insulin resistance may be associated with laminitis. Additionally or alternatively, insulin resistance may be associated with vascular dysfunction. Additionally or alternatively, insulin resistance may be associated with hypertension. Additionally or alternatively, insulin resistance may be associated with hyperadrenocorticism. Additionally or alternatively, insulin resistance may be associated with hepatic lipidosis. Laminitis, vascular dysfunction, hypertension, hyperadrenocorticism and/or hepatic lipidoses are clinical condition/signs associated with EMS and/or PPID. Thus, additionally or alternatively, insulin resistance may be associated with EMS and/or PPID.

The metabolic disorder may be hyperinsulinemia. Hyperinsulinemia may be associated with a further metabolic disorder or clinical condition/sign, e.g. hyperinsulinemia may be associated with obesity and/or regional adiposity.

Additionally or alternatively, hyperinsulinemia may be associated with laminitis. Additionally or alternatively, hyperinsulinemia may be associated with vascular dysfunction. Additionally or alternatively, hyperinsulinemia may be associated with hypertension. Additionally or alternatively, hyperinsulinemia may be associated with hepatic lipidosis. Laminitis, vascular dysfunction, hypertension and/or hepatic lipidoses are clinical condition/signs associated with EMS and/or PPID. Thus or alternatively, hyperinsulinemia may be associated with EMS and/or PPID.

In preferred embodiments, the metabolic disorder may be insulin resistance, hyperinsulinemia and/or a clinical condition/sign associated with insulin resistance and/or hyperinsulinemia. Treatment or prevention of a metabolic disorder of an equine animal in accordance with the invention may be treatment or prevention of insulin resistance and/or hyperinsulinemia.

Clinical conditions/signs associated with insulin resistance and/or hyperinsulinemia are e.g., impaired glucose tolerance, dyslipidemia, dysadipokinemia, subclinical inflammation, systemic inflammation, low grade systemic inflammation, which also comprises adipose tissue, obesity and/or regional adiposity. Treatment and/or prevention of a metabolic disorder of an equine animal in accordance with the invention may be the treatment and/or prevention of impaired glucose tolerance, dyslipidemia, dysadipokinemia, subclinical inflammation, systemic inflammation, low grade systemic inflammation, which also comprises adipose tissue, obesity and/or regional adiposity in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition/sign, e.g., a metabolic disorder or clinical condition/sign associated with insulin resistance and/or hyperinsulinemia may be impaired glucose tolerance. Hence, the treatment or prevention of a metabolic disorder of an equine animal in accordance with the invention may be the treatment or prevention of impaired glucose tolerance, preferably associated with insulin resistance and/or hyperinsulinemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition/sign, e.g., a metabolic disorder or clinical condition/sign associated with insulin resistance and/or hyperinsulinemia may be dyslipidemia. Hence, the treatment and/or prevention of a metabolic disorder of an equine animal in accordance with the invention may be the treatment and/or prevention of dyslipidemia, preferably associated with insulin resistance and/or hyperinsulinemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition/sign, e.g., a metabolic disorder or clinical condition/sign associated with insulin resistance and/or hyperinsulinemia may be dysadipokinemia. Hence, the treatment and/or prevention of a metabolic disorder of an equine animal in accordance with the invention may be treatment and/or prevention of dysadipokinemia, preferably associated with insulin resistance and/or hyperinsulinemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition/sign, e.g., a metabolic disorder or clinical condition/sign associated with insulin resistance and/or hyperinsulinemia may be subclinical inflammation or systemic inflammation, in particular low grade systemic inflammation, which also comprises adipose tissue. Hence, the treatment and/or prevention of a metabolic disorder of an equine animal in accordance with the invention may be treatment and/or prevention of subclinical inflammation or systemic inflammation, in particular low grade systemic inflammation, which also comprises adipose tissue, preferably associated with insulin resistance and/or hyperinsulinemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition/sign, e.g., a metabolic disorder or clinical condition/sign associated with insulin resistance and/or hyperinsulinemia may be obesity. Hence, the treatment and/or prevention of a metabolic disorder of an equine animal in accordance with the invention may be treatment and/or prevention of obesity, preferably associated with insulin resistance and/or hyperinsulinemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition/sign, e.g., a metabolic disorder or clinical condition/sign associated with insulin resistance and/or hyperinsulinemia may be regional adiposity. Hence, the treatment and/or prevention of a metabolic disorder of an equine animal in accordance with the invention may be treatment and/or prevention of regional adiposity, preferably associated with insulin resistance and/or hyperinsulinemia in an equine animal. That equine animal may also suffer from laminitis, vascular dysfunction, hypertension, hepatic lipidosis, atherosclerosis, hyperadrenocorticism, PPID and/or EMS.

Herein, a metabolic disorder or clinical condition/sign, e.g., a metabolic disorder or clinical condition/sign associated with insulin resistance and/or hyperinsulinemia, may be laminitis. In some embodiments, laminitis may be associated with obesity and/or regional adiposity. In some embodiments, when a metabolic disorder or clinical condition/sign is laminitis, the equine animal is suffering from EMS and/or PPID. The present invention preferably prevents the development and/or recurrence of laminitis, e.g., in an equine animal suffering from EMS and/or PPID.

Herein, a metabolic disorder or clinical condition/sign, e.g., a metabolic disorder or clinical condition/sign associated with insulin resistance and/or hyperinsulinemia, may be vascular dysfunction, e.g., vascular dysfunction in an equine animal's hoof. In some embodiments, vascular dysfunction may be associated with obesity and/or regional adiposity. In some embodiments, when a metabolic disorder or clinical condition/sign is vascular dysfunction, the equine animal is suffering from EMS and/or PPID. The present invention preferably prevents the development and/or recurrence of vascular dysfunction, e.g., in an equine animal suffering from EMS and/or PPID.

Herein, a metabolic disorder or clinical condition/sign, e.g., a metabolic disorder or clinical condition/sign associated with insulin resistance and/or hyperinsulinemia, may be hypertension. In some embodiments, hypertension may be associated with regional obesity and/or regional adiposity. In some embodiments, when a metabolic disorder or clinical condition/sign is hypertension, the equine animal is suffering from EMS and/or PPID. The present invention preferably prevents the development and/or recurrence of hypertension, e.g., in an equine animal suffering from EMS and/or PPID.

Herein, a metabolic disorder or clinical condition/sign, e.g., a metabolic disorder or clinical condition/sign associated with insulin resistance and/or hyperinsulinemia, may be hepatic lipidosis. In some embodiments, hepatic lipidosis may be associated with regional obesity and/or regional adiposity. In some embodiments, when a metabolic disorder or clinical condition/sign is hepatic lipidosis, the equine animal is suffering from EMS and/or PPID. The present invention preferably prevents the development and/or recurrence of hepatic lipidosis, e.g., in an equine animal suffering from EMS and/or PPID.

Herein, a metabolic disorder or clinical condition/sign, e.g., a metabolic disorder or clinical condition/sign associated with insulin resistance and/or hyperinsulinemia, may be atherosclerosis, In some embodiments, atherosclerosis may be associated with systemic inflammation, subclinical inflammation, low grade systemic inflammation, which also comprises adipose tissue. In some embodiments, when a metabolic disorder or clinical condition/sign is atherosclerosis, the equine animal is suffering from EMS and/or PPID. The present invention preferably prevents the development and/or recurrence of atherosclerosis, e.g., in an equine animal suffering from EMS and/or PPID.

Herein, a metabolic disorder or clinical condition/sign, e.g., a metabolic disorder or clinical condition/sign associated with insulin resistance and/or hyperinsulinemia, may be hyperadrenocorticism. In some embodiments, hyperadrenocorticism may be associated with systemic inflammation, subclinical inflammation, low grade systemic inflammation, which also comprises adipose tissue. In some embodiments, when a metabolic disorder or clinical condition/sign is hyperadrenocorticism, the equine animal is suffering from EMS and/or PPID. The present invention preferably provides for the treatment and/or prevention of hyperadrenocorticism, i.e., it prevents the development and/or recurrence of hyperadrenocorticism, e.g., in an equine animal suffering from EMS and/or PPID.

Herein, a metabolic disorder or clinical condition/sign, e.g., a metabolic disorder or clinical condition/sign associated with insulin resistance and/or hyperinsulinemia, may be Equine Metabolic Syndrome (EMS). In some embodiments, EMS may be associated with obesity and/or regional adiposity.

Herein, a metabolic disorder or clinical condition/sign, e.g., a metabolic disorder or clinical condition/sign associated with insulin resistance and/or hyperinsulinemia, may be Equine Pituitary Pars Intermedia Dysfunction (PPID). In some embodiments, PPID may be associated with hyperadrenocorticism.

In some embodiments, the equine animal treated in accordance with the invention (e.g., for hyperinsulinemia, insulin resistance, and/or a clinical condition/sign associated with insulin resistance and/or hyperinsulinemia) is suffering from laminitis, vascular dysfunction, PPID and/or EMS.

In some embodiments, impaired glucose tolerance may be associated with obesity and/or regional adiposity. Hence, the treatment and/or prevention of a metabolic disorder of an equine animal in accordance with the invention may be treatment and/or prevention of impaired glucose tolerance associated with obesity and/or regional adiposity in an equine animal.

In some embodiments, impaired glucose tolerance may be associated with hyperadrenocorticism. Hence, the treatment and/or prevention of a metabolic disorder of an equine animal in accordance with the invention may be treatment and/or prevention of impaired glucose tolerance associated with hyperadrenocorticism in an equine animal.

Insulin resistance can be described as the condition in which normal amounts of insulin are inadequate to produce a normal insulin response from fat, muscle and liver cells. Insulin resistance in fat cells reduces the effects of insulin and results in elevated hydrolysis of stored triglycerides in the absence of measures which either increase insulin sensitivity or which provide additional insulin. Increased mobilization of stored lipids in these cells elevates free fatty acids in the blood plasma. Insulin resistance in muscle cells reduces glucose uptake (and so local storage of glucose as glycogen), whereas insulin resistance in liver cells results in impaired glycogen synthesis and a failure to suppress glucose production. Elevated blood fatty acid levels, reduced muscle glucose uptake, and increased liver glucose production, may all contribute to elevated blood glucose levels (hyperglycemia), although hyperglycemia is not a major issue e.g., in insulin-resistant horses. In the horse, when insulin-resistant target tissues, e.g., skeletal muscle, have a reduced capacity for glucose uptake, the pancreas is stimulated to release more insulin, leading to hyperinsulinemia.

Surrogate indices of insulin sensitivity may be calculated according to the QUICKI (quantitative insulin sensitivity check index: 1/log(glucose*insulin)) for basal blood level. For dynamic testings, e.g. during a glucose challenge a modified Belfiore Index (1/log($\Delta$AUC-glucose*$\Delta$AUC-insulin)) can be employed.

Insulin resistance may be present in association with regional adiposity, e.g., cresty neck, tail fat depots, visceral adiposity, hypertension and dyslipidemia involving elevated triglycerides, small dense low-density lipoprotein (sdLDL) particles, and decreased HDL cholesterol levels. With respect to visceral adiposity, a great deal of evidence in humans suggests two strong links with insulin resistance. First, unlike subcutaneous adipose tissue, visceral adipose cells produce significant amounts of proinflammatory cytokines such as tumor necrosis factor-alpha (TNF-$\alpha$), and Interleukins-1 and -6, etc. In numerous experimental models, these proinflammatory cytokines profoundly disrupt normal insulin action in fat and muscle cells, and may be a major factor in causing the whole-body insulin resistance observed in human patients with visceral adiposity. Similar, in equines the different excessive regional fat depots contribute to low grade systemic inflammation. Second, adiposity is related to an accumulation of fat in the liver, a condition known as nonalcoholic fatty liver disease (NAFLD) in humans and hepatic lipidosis in general terms, e.g., in equines. The result of NAFLD is an excessive release of free fatty acids into the bloodstream (due to increased lipolysis), and an increase in hepatic glucose production, both of which have the effect of exacerbating peripheral insulin resistance. The cause of the vast majority of cases of insulin resistance remains unknown. There is clearly an inherited component. However, there are some grounds for suspecting that insulin resistance is related to a high-carbohydrate diet. Inflammation also seems to be implicated in causing insulin resistance.

Hyperinsulinemia may be described as a condition in which there are excess levels, i.e., more than about 10-20 µIU/mL of insulin circulating in the blood. As mentioned, it is commonly present in cases of, and may be a consequence of, insulin resistance in equine animals.

Impaired glucose tolerance can be described as condition in which the response to a after a glycemic challenge e.g., after a meal or after a loading test (glucose tolerance test) the glycemic peak of the glucose excursion is higher and/or the duration of the glucose excursion is prolonged.

Dyslipidemia or hyperlipidemia is the presence of raised or abnormal levels of lipids and/or lipoproteins in the blood. Lipid and lipoprotein abnormalities are regarded as a highly modifiable risk factor for cardiovascular disease due to the influence of cholesterol, one of the most clinically relevant lipid substances, on atherosclerosis. Glycerol is a precursor for the synthesis of triacylglycerols (triglycerides) and of phospholipids in the liver and adipose tissue. When the body uses stored fat as a source of energy, glycerol and fatty acids are released into the bloodstream after hydrolysis of the triglycerides. The glycerol component can be converted to glucose by the liver and provides energy for cellular metabolism. Normal levels of free fatty acids in the blood equine animals are concentrations of 50 to 100 mg/dl (0.6 to 1.2 mmol/1). Normal levels of triglycerides are e.g., up to around 50 mg/dL. Normal levels of blood cholesterol are, e.g., around 120 mg/dl for the horse.

Dysadipokinemia can be described as a condition in which the circulating plasma levels of biologically active substances produced in adipose tissue that act in an autocrine/paracrine or endocrine fashion is deviated. e.g., an elevation of leptin and/or a reduction of adiponectin.

Subclinical inflammation or systemic inflammation, in particular low grade systemic inflammation is characterized by increased expression and secretion of proinflammatory cytokines such as tumor necrosis factor-alpha and/or lower expression and secretion of anti-inflammatory cytokines e.g., interleukin-10 and/or their respective receptors.

Laminitis can be described as an inflammation or edema of the sensitive laminae of the hoof resulting e.g., in lameness. The laminae bond the hoof wall to the pedal bone, which supports the entire weight of the horse or equine. Severe cases of laminitis can result in the pedal bone rotation that may progress to perforation of the sole. Laminitis induced lameness can be graded e.g., by visual score of behavior in standing position and moving performance.

Vascular dysfunction can be described as impaired action of endothelium-dependent insulin induced vasodilation, as well alteration of direct insulin effects on vascular smooth muscles, e.g., relaxation and reactivity to vasoconstrictor stimuli.

Equine Metabolic Syndrome is defined by the presence of insulin resistance, obesity and/or regional adiposity. The EMS phenotype may also comprise dyslipidemia, dyadipokinemia and/or hypertension. The syndrome can be described as a combination of medical disorders that increase the risk of developing associated pathologies, e.g., laminitis. The equine metabolic syndrome might also be associated with other disorders like hepatic lipidosis or infertility.

Obesity can be described as a medical condition in which excess body fat has accumulated to the extent that it may have an adverse effect on health, leading to reduced life expectancy. In equines e.g., during physical examination body condition scores of equal or more than 7 (out of 9) are encountered.

Regional adiposity in equine animals can be described as a medical condition in which body fat (adipose tissue) accumulates in specific regions, e.g., the neck (cresty neck), either side of the tailhead, prepuce, in fat pads in the rump area, the mammary gland region, and/or in supraorbital fat pads. Regional adiposity also encompasses visceral adiposity, e.g., increased omental fat.

Obesity and or regional adiposity is associated with many other diseases, particularly heart disease, type 2 diabetes (though this is rare in horses), certain types of cancer, osteoarthritis and/or strangulating lipoma. Obesity is most commonly caused by a combination of excessive dietary calories, lack of physical activity, and genetic susceptibility, though a limited number of cases are due to a single cause, e.g., solely to genetics.

Atherosclerosis can be described as a condition in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

Pituitary Pars Intermedia Dysfunction (PPID) is a common disease of older horses and ponies. Hypothalamic dopaminergic neurodegeneration results in an elevated adrenocorticotropic hormone (ACTH) production in the Pituitary Pars Intermedia and leads to hyperadrenocorticism. Clinical signs include hirsutism (a long, often curly coat that may not shed), polydipsia/polyuria, excessive sweating, weight loss, muscle wasting, regional fat deposits, lethargy, infections e.g., sinusitis and/or laminitis.

Equine animals. Herein, the term "equine animal" may be used interchangeably with the term "equine" and encompasses any member of the genus *Equus*. It encompasses, e.g., any horse or pony, the taxonomic designations *Equus ferus* and/or *Equus caballus*, and/or the subspecies *Equus ferus caballus*. The equine animal may, e.g., be a domestic horse.

Pharmaceutically acceptable forms. Herein, references to SGLT2 inhibitors and/or their use according to the invention encompass pharmaceutically acceptable forms of the SGLT2 inhibitors, unless otherwise stated.

According to the invention, any pharmaceutically acceptable form of the SGLT2 inhibitor, e.g., of formula (1), preferably formula (18), more preferably formula (2), may be used. E.g., a crystalline form may be used. Prodrug forms are also encompassed by the present invention.

Prodrug forms may include, e.g., esters and/or hydrates. The term prodrug is also meant to include any covalently bonded carrier which releases the active compound of the invention in vivo when the prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention.

Crystalline forms for use according to the invention include a complex of one or more SGLT2 inhibitors with one or more amino acids (see e.g., WO 2014/016381). An amino acid for such use may be a natural amino acid. The amino acid may be a proteogenic amino acid (including L-hydroxyproline), or a non-proteogenic amino acid. The amino acid may be a D- or an L-amino acid. In some preferred embodiments the amino acid is proline (L-proline and/or D-proline, preferably L-proline). E.g., a crystalline complex of 1-cyano-2-(4-cyclopropyl-benzyl)-4-((3-D-glucopyranos-1-yl)-benzene (formula (2); compound A) with proline (e.g. L-proline) is preferred.

Thus, herein is disclosed a crystalline complex between one or more natural amino acids and an SGLT2 inhibitor, e.g., a crystalline complex between one or more natural amino acids and a glucopyranosyl-substituted benzene derivative SGLT2 inhibitor, preferably a SGLT2 inhibitor of formula (1), more preferably of formula (18) or yet more preferably of formula (2) (compound A). Thus, herein is disclosed a crystalline complex between one or more natural amino acids and 1-cyano-2-(4-cyclopropyl-benzyl)-4-(β-D-glucopyranos-1-yl)-benzene (compound A).

Further disclosed herein is the use of one or more crystalline complexes as defined hereinbefore or hereinafter for preparing a pharmaceutical composition which is suitable for the treatment or prevention of diseases or conditions which can be influenced by inhibiting sodium-dependent glucose co-transporter SGLT, preferably SGLT2. Further disclosed herein is the use of one or more crystalline complexes as defined hereinbefore or hereinafter for preparing a pharmaceutical composition for inhibiting the sodium-dependent glucose co-transporter SGLT2.

A crystalline complex between one or more natural amino acids (e.g. proline, preferably L-proline) and an SGLT2 inhibitor, is a preferred pharmaceutically acceptable form of a SGLT2 inhibitor for use according to the present invention. In particular, a crystalline complex between one or more natural amino acids (e.g. proline, preferably L-proline) and a glucopyranosyl-substituted benzene derivative SGLT2 inhibitor, preferably a SGLT2 inhibitor of formula (1), more preferably of formula (18) or yet more preferably of formula (2) (compound A) is a preferred pharmaceutically acceptable form of a SGLT2 inhibitor for use according to the present invention. A crystalline complex between one or more natural amino acids (e.g., proline, preferably L-proline) and 1-cyano-2-(4-cyclopropyl-benzyl)-4-(β-D-glucopyranos-1-yl)-benzene (compound A) is particularly preferred as a pharmaceutically acceptable form of a SGLT2 inhibitor for use according to the present invention.

Also disclosed herein is a method for making one or more crystalline complexes as defined hereinbefore and hereinafter, said method comprising the following steps:
  a. preparing a solution of the one or more SGLT2 inhibitors (e.g., a glucopyranosyl-substituted benzene derivative, or a SGLT2 inhibitor of formula (1), preferably formula (18) or more preferably formula (2), i.e., compound A) and the one or more natural amino acids in a solvent or a mixture of solvents;
  b. storing the solution to precipitate the crystalline complex out of solution;
  c. removing the precipitate from the solution; and
  d. drying the precipitate optionally until any excess of said solvent or mixture of solvents has been removed.

A certain pharmaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g., by grinding. Since breakdown of the pharmaceutically active substance as a side effect of the grinding (or micronizing) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation which always contains the specified amount of active substance in a reproducible manner.

Another problem which may arise in the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

The absorption of moisture reduces the content of pharmaceutically active substance as a result of the increased weight caused by the uptake of water. Pharmaceutical compositions with a tendency to absorb moisture have to be protected from moisture during storage, e.g., by the addition of suitable drying agents or by storing the drug in an environment where it is protected from moisture. Preferably, therefore, a pharmaceutically active substance should be at best slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

A crystalline complex between a natural amino acid and one or more SGLT2 inhibitors (e.g. a glucopyranosyl-substituted benzene derivative or a SGLT2 inhibitor of formula (1), or formula (18) or, particularly, of formula (2), i.e. compound A) fulfills important requirements mentioned hereinbefore.

Preferably the natural amino acid is present in either its (D) or (L) enantiomeric form, most preferably as the (L) enantiomer.

Furthermore those crystalline complexes according to this invention are preferred which are formed between the one or more SGLT2 inhibitors (e.g. of formula (1), preferably formula (18) or, particularly, of formula (2), i.e. compound A) and one natural amino acid, most preferably between the compound A and the (L) enantiomer of a natural amino acid.

Preferred amino acids according to this invention are selected from the group consisting of phenylalanine and proline, in particular (L)-proline and (L)-phenylalanine.

According to a preferred embodiment the crystalline complex is characterized in that the natural amino acid is proline, in particular (L)-proline.

Preferably the molar ratio of the one or more SGLT2 inhibitors (e.g. of formula (1), preferably formula (18) or, particularly, of formula (2), i.e. compound A) and the natural amino acid is in the range from about 2:1 to about 1:3; more preferably from about 1.5:1 to about 1:1.5, even more preferably from about 1.2:1 to about 1:1.2, most preferably about 1:1. In the following such an embodiment is referred to as "complex (1:1)" or "1:1 complex".

Therefore a preferred crystalline complex according to this invention is a complex (1:1) between said SGLT2 inhibitor (e.g. of formula (1), preferably formula (18) or, particularly, of formula (2), i.e. compound A) and proline; in particular of said SGLT2 inhibitor and L-proline.

According to a preferred embodiment the crystalline complex, in the particular the 1:1 complex of said SGLT2 inhibitor with L-proline, is a hydrate.

Preferably the molar ratio of the crystalline complex and water is in the range from about 1:0 to 1:3; more preferably from about 1:0 to 1:2, even more preferably from about 1:0.5 to 1:1.5, most preferably about 1:0.8 to 1:1.2, in particular about 1:1.

The crystalline complex of said SGLT2 inhibitor with proline, in particular with L-proline and water, may be identified and distinguished from other crystalline forms by means of their characteristic X-ray powder diffraction (XRPD) patterns.

For example, a crystalline complex of compound A with L-proline is preferably characterized by an X-ray powder diffraction pattern that comprises peaks at 20.28, 21.14 and 21.64 degrees 2Θ (±0.1 degrees 2Θ), wherein said X-ray powder diffraction pattern is made using CuK$_{\alpha 1}$ radiation.

In particular said X-ray powder diffraction pattern comprises peaks at 4.99, 20.28, 21.14, 21.64 and 23.23 degrees 2Θ (±0.1 degrees 2Θ), wherein said X-ray powder diffraction pattern is made using CuK$_{\alpha 1}$ radiation.

More specifically said X-ray powder diffraction pattern comprises peaks at 4.99, 17.61, 17.77, 20.28, 21.14, 21.64, 23.23 and 27.66 degrees 2Θ (±0.1 degrees 2Θ), wherein said X-ray powder diffraction pattern is made using CuK$_{\alpha 1}$ radiation.

Even more specifically said X-ray powder diffraction pattern comprises peaks at 4.99, 15.12, 17.61, 17.77, 18.17, 20.28, 21.14, 21.64, 23.23 and 27.66 degrees 2Θ (±0.1 degrees 2Θ), wherein said X-ray powder diffraction pattern is made using CuK$_{\alpha 1}$ radiation.

Even more specifically, the crystalline complex of compound A and L-proline is characterized by an X-ray powder diffraction pattern, made using CuK$_{\alpha 1}$ radiation, which comprises peaks at degrees 2Θ (±0.1 degrees 2Θ) as contained in Table 1.

TABLE 1

X-ray powder diffraction pattern of the crystalline complex of compound A and L-proline (only peaks up to 30° in 2 Θ are listed):

| 2 Θ [°] | d-value [Å] | Intensity I/I$_0$ [%] |
| --- | --- | --- |
| 4.99 | 17.68 | 39 |
| 7.01 | 12.61 | 6 |
| 8.25 | 10.70 | 11 |
| 9.95 | 8.88 | 12 |
| 13.15 | 6.73 | 30 |
| 13.33 | 6.64 | 10 |
| 14.08 | 6.28 | 4 |
| 15.12 | 5.85 | 32 |
| 16.40 | 5.40 | 12 |
| 16.49 | 5.37 | 13 |
| 17.11 | 5.18 | 6 |
| 17.61 | 5.03 | 32 |
| 17.77 | 4.99 | 35 |
| 18.17 | 4.88 | 32 |
| 18.32 | 4.84 | 28 |
| 18.72 | 4.74 | 8 |
| 19.16 | 4.63 | 30 |
| 19.96 | 4.45 | 26 |
| 20.28 | 4.37 | 56 |
| 20.60 | 4.31 | 7 |
| 21.14 | 4.20 | 84 |
| 21.64 | 4.10 | 100 |
| 22.33 | 3.98 | 15 |
| 23.23 | 3.83 | 41 |
| 24.06 | 3.70 | 4 |
| 24.51 | 3.63 | 15 |
| 24.93 | 3.57 | 26 |
| 25.89 | 3.44 | 23 |
| 26.21 | 3.40 | 11 |
| 26.84 | 3.32 | 8 |
| 27.66 | 3.22 | 38 |
| 27.96 | 3.19 | 9 |
| 28.26 | 3.16 | 5 |
| 28.44 | 3.14 | 6 |
| 28.75 | 3.10 | 6 |
| 29.18 | 3.06 | 19 |

Even more specifically, said crystalline complex is characterized by an X-ray powder diffraction pattern, made using CuK$_{\alpha 1}$ radiation, which comprises peaks at degrees 2Θ (±0.1 degrees 2Θ as shown in FIG. 13.

Furthermore said crystalline complex of the compound A with L-proline is characterized by a melting point of above 89° C., in particular in a range from about 89° C. to about 115° C., more preferably in a range from about 89° C. to about 110° C. (determined via DSC; evaluated as onset-temperature; heating rate 10 K/min). It can be observed that this crystalline complex melts under dehydration. The obtained DSC curve is shown in FIG. 14.

Said crystalline complex of the compound A with L-proline shows a weight loss by thermal gravimetry (TG). The observed weight loss indicates that the crystalline form contains water which may be bound by adsorption and/or may be part of the crystalline lattice, i.e., the crystalline form may be present as a crystalline hydrate. The content of water in the crystalline form lies in the range from 0 to about 10 weight-%, in particular 0 to about 5 weight-%, even more preferably from about 1.5 to about 5 weight-%. The dotted line depicts a weight loss of between 2.8 and 3.8% of water. From the observed weight loss a stoichiometry close to a monohydrate can be estimated.

Said crystalline complex has advantageous physicochemical properties which are beneficial in the preparation of a pharmaceutical composition. In particular the crystalline complex has a high physical and chemical stability under various environmental conditions and during the production of a medicament. For example the crystals can be obtained in a shape and particle size which are particular suitable in a production method for solid pharmaceutical formulations. In addition the crystals show a high mechanical stability that allows grinding of the crystals. Furthermore the crystalline complex does not show a high tendency to absorb moisture and is chemically stable, i.e., the crystalline complex allows the production of a solid pharmaceutical formulation with a long shelf life. On the other hand the crystalline complex has a favorably high solubility over a wide pH-range which is advantageous in solid pharmaceutical formulations for oral administration.

The X-ray powder diffraction patterns may be recorded using a STOE-STADI P-diffractometer in transmission mode fitted with a location-sensitive detector (OED) and a Cu-anode as X-ray source (CuK$_{\alpha 1}$ radiation, $\lambda$=1.54056 Å, 40 kV, 40 mA). In Table 1 the values "2Θ [°]" denote the angle of diffraction in degrees and the values "d [Å]" denote the specified distances in Å between the lattice planes. The intensity shown in FIG. 13 is given in units of cps (counts per second).

In order to allow for experimental error, the above described 2 Θ values should be considered accurate to ±0.1 degrees 2 Θ, in particular ±0.05 degrees 2 Θ. That is to say, when assessing whether a given sample of crystals of the compound A is the crystalline form in accordance with the above described 2 Θ values, a 2 Θ value which is experimentally observed for the sample should be considered identical with a characteristic value described above if it falls within ±0.1 degrees 2 Θ of the characteristic value, in particular if it falls within ±0.05 degrees 2 Θ of the characteristic value.

The melting point is determined by DSC (Differential Scanning calorimetry) using a DSC 821 (Mettler Toledo). The weight loss is determined by thermal gravimetry (TG) using a TGA 851 (Mettler Toledo).

Also disclosed herein is a method for making a crystalline complex as defined hereinbefore and hereinafter, said method comprising the following steps:
 a. preparing a solution of one or more SGLT2 inhibitors as described herein (e.g. compound A or another SGLT2 inhibitor described herein) and the one or more natural amino acids in a solvent or a mixture of solvents;
 b. storing the solution to precipitate the crystalline complex out of solution;
 c. removing the precipitate from the solution; and
 d. drying the precipitate optionally until any excess of said solvent or mixture of solvents has been removed.

According to step (a) a solution of the one or more SGLT2 inhibitors (e.g., compound A or another SGLT2 inhibitor described herein) and the one or more natural amino acids in a solvent or a mixture of solvents is prepared. Preferably the solution is saturated or at least nearly saturated or even supersaturated with respect to the crystalline complex. In the step (a) the one or more SGLT2 inhibitors may be dissolved in a solution comprising the one or more natural amino acids or the one or more natural amino acids may be dissolved in a solution comprising the SGLT2 inhibitor. According to an alternative procedure the one or more SGLT2 inhibitors is dissolved in a solvent or mixture of solvents to yield a first solution and the one or more natural amino acids are dissolved in a solvent or mixture of solvents to yield a second solution. Thereafter said first solution and said second solution are combined to form the solution according to step (a).

Preferably the molar ratio of the natural amino acid and the one or more SGLT2 inhibitors (e.g., compound A or any other SGLT2 inhibitor described herein) in the solution corresponds to the molar ratio of the natural amino acid and the one or more SGLT2 inhibitors in the crystalline complex to be obtained. Therefore a preferred molar ratio is in the range from about 1:2 to 3:1; most preferably about 1:1.

Suitable solvents are preferably selected from the group consisting of $C_{1-4}$-alkanols, water, ethyl acetate, acetonitrile, acetone, diethyl ether, tetrahydrofuran, and mixture of two or more of these solvents.

More preferred solvents are selected from the group consisting of methanol, ethanol, isopropanol, water and mixture of two or more of these solvents, in particular mixtures of one or more of said organic solvents with water.

Particularly preferred solvents are selected from the group consisting of ethanol, isopropanol, water and mixtures of ethanol and/or isopropanol with water.

In case a mixture of water and one or more $C_{1-4}$-alkanols, in particular of methanol, ethanol and/or isopropanol, most preferably of ethanol, is taken, a preferred volume ratio of water:the alkanol is in the range from about 99:1 to 1:99; more preferably from about 50:1 to 1:80; even more preferably from about 10:1 to 1:60.

Preferably the step (a) is carried out at about room temperature (about 20° C.) or at an elevated temperature up to about the boiling point of the solvent or mixture of solvents used.

According to a preferred embodiment the starting material of the one or more SGLT2 inhibitors (e.g., compound A or any other SGLT2 inhibitor described herein) and/or of the one or more natural amino acids and/or of the solvent and mixtures of solvents contain an amount of $H_2O$ which is at least the quantity required to form a hydrate of the SGLT2 inhibitor; in particular at least 1 mol, preferably at least 1.5 mol of water per mol of SGLT2 inhibitor. Even more preferably the amount of water is at least 2 mol of water per mol of SGLT2 inhibitor. This means that either the one or more SGLT2 inhibitors (e.g., compound A) as starting material or the one or more natural amino acids or said solvent or mixture of solvents, or said compounds and/or solvents in combination contain an amount of $H_2O$ as specified above. For example if the starting material of the one or more SGLT2 inhibitors (e.g., compound A) or of the natural amino acid in step (a) does contain sufficient water as specified above, a water content of the solvent(s) is not mandatory.

In order to reduce the solubility of the crystalline complex according to this invention in the solution, in step (a) and/or in step (b) one or more antisolvents may be added, preferably during step (a) or at the beginning of step (b). Water is an example of a suitable antisolvent. The amount of antisolvent is preferably chosen to obtain a supersaturated or saturated solution with respect to the crystalline complex.

In step (b) the solution is stored for a time sufficient to obtain a precipitate, i.e., the crystalline complex. The temperature of the solution in step (b) is about the same as or lower than in step (a). During storage the temperature of the solution is preferably lowered, preferably to a temperature in the range of 20° C. to 0° C. or even lower. The step (b) can be carried out with or without stirring. As known to the one skilled in the art by the period of time and the difference of temperature in step (b) the size, shape and quality of the obtained crystals can be controlled. Furthermore the crystallization may be induced by methods as known in the art, for example by mechanical means such as scratching or rubbing the contact surface of the reaction vessel for example with a glass rod. Optionally the (nearly) saturated or supersaturated solution may be inoculated with seed crystals.

In step (c) the solvent(s) can be removed from the precipitate by known methods as for example by filtration, suction filtration, decantation or centrifugation.

In step (d) an excess of the solvent(s) is removed from the precipitate by methods known to the one skilled in the art as for example by reducing the partial pressure of the solvent(s), preferably in vacuum, and/or by heating above ca. 20° C., preferably in a temperature range below 100° C., even more preferably below 85° C.

Compound A may be synthesized by methods as specifically and/or generally described or cited in international application WO2007/128749 (ref. 18) which in its entirety is incorporated herein by reference, and/or in the Examples disclosed herein below. Biological properties of the compound A may also be investigated as is described in WO2007/128749 (ref. 18).

A crystalline complex as described herein is preferably employed as drug active substance in substantially pure form, that is to say, essentially free of other crystalline forms of the one or more SGLT2 inhibitors (e.g., compound A). Nevertheless, the invention also embraces a crystalline complex in admixture with another crystalline form or forms. Should the drug active substance be a mixture of crystalline forms, it is preferred that the substance comprises at least 50%-weight, even more preferably at least 90%-weight, most preferably at least 95%-weight of the crystalline complex as described herein.

In view of its ability to inhibit SGLT activity, a crystalline complex according to the invention is suitable for the use in the treatment and/or preventive treatment of conditions or diseases which may be affected by the inhibition of SGLT activity, particularly SGLT-2 activity, in particular the metabolic disorders as described herein. The crystalline complex according to the invention is also suitable for the preparation of pharmaceutical compositions for the treatment and/or preventive treatment of conditions or diseases which may be affected by the inhibition of SGLT activity, particularly SGLT-2 activity, in particular metabolic disorders as described herein. A crystalline complex as described herein (in particular of compound A with a natural amino acid, e.g., proline, particularly L-proline) is also suitable for the use in the treatment of equine.

Pharmaceutical Compositions and Formulations

SGLT2 inhibitors for use according to the invention may be prepared as pharmaceutical compositions. They may be prepared as solid or as liquid formulations. In either case, they are preferably prepared for oral administration, preferably in liquid form for oral administration. The SGLT2 inhibitors may, however, also be prepared, e.g., for parenteral administration.

Solid formulations include tablets, granular forms, and other solid forms such as suppositories. Among solid formulations, tablets and granular forms are preferred.

Pharmaceutical compositions within the meaning of the present invention may comprise one or more SGLT2 inhibitors according to the present invention and one or more excipients. Any excipient that allows for, or supports, the intended medical effect may be used. Such excipients are available to the skilled person. Useful excipients are for example anti-adherents (used to reduce the adhesion between the powder (granules) and the punch faces and thus prevent sticking to tablet punches), binders (solution binders or dry binders that hold the ingredients together), coatings (to protect tablet ingredients from deterioration by moisture in the air and make large or unpleasant-tasting tablets easier to swallow), disintegrants (to allow the tablet to break upon dilution), fillers, diluents, flavors, colors, glidants (flow regulators—to promote powder flow by reducing interparticle friction and cohesion), lubricants (to prevent ingredients from clumping together and from sticking to the tablet punches or capsule filling machine), preservatives, sorbents, sweeteners, etc.

Formulations according to the invention, e.g., solid formulations, may comprise carriers and/or disintegrants selected from the group of sugars and sugar alcohols, e.g., mannitol, lactose, starch, cellulose, microcrystalline cellulose and cellulose derivatives, e. g., methylcellulose, and the like.

Manufacturing procedures for formulations suitable for equine animals are known to the person skilled in the art, and for solid formulations comprise, e.g., direct compression, dry granulation and wet granulation. In the direct compression process, the active ingredient and all other excipients are placed together in a compression apparatus that is directly applied to press tablets out of this material. The resulting tablets can optionally be coated afterwards in order to protect them physically and/or chemically, e.g., by a material known from the state of the art.

A unit for administration, e.g., a single liquid dose or a unit of a solid formulation, e.g., a tablet, may comprise 5 to 2500 mg, or e.g. 5 to 2000 mg, 5 mg to 1500 mg, 10 mg to 1500 mg, 10 mg to 1000 mg, or 10-500 mg of one or more SGLT2 inhibitors for use according to the invention. As the skilled person would understand, the content of the one or more SGLT2 inhibitors in a solid formulation, or any formulation as disclosed herein for administration to an equine animal, may be increased or decreased as appropriate in proportion to the body weight of the equine animal to be treated.

In one embodiment a pharmaceutical composition for use according to the invention is designed for oral or parenteral administration, preferably for oral administration. The oral administration may be ameliorated by excipients which modify the smell and/or haptic properties of the pharmaceutical composition for the intended patient.

When the one or more SGLT2 inhibitors for use according to the invention is formulated for oral administration, it is preferred that excipients confer properties, e.g., palatability and/or chewability that render the formulation suitable for administration to an equine animal.

Also preferred are liquid formulations. Liquid formulations may be, e.g., solutions, syrups or suspensions. They may be administered directly to the equine animal or may be mixed with the food and/or drink (e.g., drinking water, or the like) of the equine animal. One advantage of a liquid formulation (similar to a formulation in granular form), is that such a dosage form allows precise dosing. For example, the one or more SGLT2 inhibitors may be dosed precisely in proportion to the body mass of an equine animal. Typical compositions of liquid formulations are known to the person skilled in the art.

Dosing and Administration

A practitioner skilled in the art can determine suitable doses for the uses of the present invention. Preferred units dosing units include mg/kg, i.e., mg SGLT2 inhibitor per body mass of the equine animal. One or more SGLT2 inhibitors of the invention may, e.g., be administered in doses of 0.01-5 mg/kg bodyweight per day, e.g., 0.01-4 mg/kg, e.g., 0.01-3 mg/kg, e.g., 0.01-2 mg/kg, e.g., 0.01-1.5 mg/kg, e.g., 0.01-1 mg/kg, e.g. 0.01-0.75 mg/kg, e.g., 0.01-0.5 mg/kg, e.g., 0.01-0.4 mg/kg, e.g., 0.01-0.4 mg/kg bodyweight per day. Preferably the dose is 0.02-0.5 mg/kg bodyweight per day, more preferably 0.03-0.4 mg/kg bodyweight per day, e.g. 0.03-0.3 mg/kg bodyweight per day.

In a preferred embodiment, the one or more SGLT2 inhibitors or a pharmaceutically acceptable form thereof may be administered in dosages of 0.01 to 3.0 mg/kg body weight per day, preferably from 0.02 to 1.0 mg/kg body weight per day, more preferably from 0.03 to 0.4 mg/kg body weight per day. Thus, the one or more SGLT2 inhibitors or pharmaceutically acceptable form thereof may be prepared for the administration of 0.01 to 3.0 mg/kg body weight per day, preferably from 0.02 to 1.0 mg/kg body weight per day, more preferably from 0.03 to 0.4 mg/kg body weight per day.

A practitioner skilled in the art is able to prepare one or more SGLT2 inhibitors of the invention for administration according to a desired dose.

Preferably, according to the invention, one or more SGLT2 inhibitors is administered no more than three times per day, more preferably no more than twice per day, most preferably only once per day. The frequency of administration can be adapted to the typical feeding rate of the equine animal.

According to the invention, an SGLT2 inhibitor, e.g., compound A, may be administered such that an appropriate blood plasma concentration of the one or more SGLT2 inhibitors is achieved (e.g., a maximal blood plasma concentration, or blood plasma concentration after a given time, e.g., 4, 8, 12 or 24 hours after oral administration, preferably about 8 hours after oral administration). E.g., for compound A, the blood plasma concentration (e.g., maximal blood plasma concentration or blood plasma concentration after said given time after oral administration) may be within the range 2 to 4000 nM, e.g. 20 to 3000 nM, or e.g., 40 to 2000 nM.

Preferably, following administration and the time required for the one or more SGLT2 inhibitors to reach the bloodstream, such levels are maintained in the blood over a time interval of at least 12 hours, more preferably at least 18 hours, most preferably at least 24 h.

Preferably, according to the invention, one or more SGLT2 inhibitors is administered orally, in liquid or solid form. The one or more SGLT2 inhibitors may be administered directly to the animals mouth (e.g., using a syringe, preferably a body-weight-graduated syringe) or together with the animal's food or drink (e.g., with its drinking water or the like), in each case preferably in liquid form. The SGLT2 inhibitors may, however, also be administered, e.g., parenterally, or by any other route of administration, e.g., rectally.

The one or more SGLT2 inhibitors may be used alone or in combination with another drug. In some embodiments, the one or more SGLT2 inhibitors are used in combination with one or more further oral antihyperglycemic drugs. When the one or more SGLT2 inhibitors is used in combination with a further drug, the one or more SGLT2 inhibitors and any further drug may be administered simultaneously, sequentially (in any order), and/or according to a chronologically staggered dosage regime. In such embodiments, when a further drug for combined administration with the one or more SGLT2 inhibitors is not administered simultaneously with the SGLT2 inhibitor, the one or more SGLT2 inhibitors and any further drug are preferably administered within a period of at least 2 weeks, 1 month, 2 months, 4 months, 6 months or longer, e.g., 12 months or more.

In some embodiments the one or more SGLT2 inhibitors (whether used alone or in combination with another drug) is not used in combination with 1-[(3-cyano-pyridin-2-yl) methyl]-3-methyl-7-(2-butyn-1-yl)-8-[3-(R)-amino-piperidin-1-yl]-xanthine or a pharmaceutically acceptable salt thereof, i.e., the equine animal is not treated with said compound. In some embodiments the one or more SGLT2 inhibitors is not used in combination with a DPP-IV inhibitor, i.e., the equine animal is not treated with a DPP-IV inhibitor.

In some embodiments, the one or more SGLT2 inhibitors are used as a monotherapy, i.e., stand-alone therapy, i.e., no other medication is administered to the equine animal for the treatment or prevention of the same metabolic disorder, i.e., the metabolic disorder for which the one or more SGLT2 inhibitors is administered. E.g., no other medication is administered to the equine animal for the treatment or prevention of the same metabolic disorder within a period of at least 2, 3, or 4 weeks before and after administration of the SGLT2 inhibitor.

BRIEF DESCRIPTION OF THE FIGURES

FIG. 15 shows the increase of plasma glucose [mM] and insulin [µIU/mL] during a glucose challenge, the delta of time "0"—before the challenge and 120 min after the challenge is given. Open columns represent the values before ("pre") treatment; filled columns give the values on day 14 of treatment ("post") with compound A (panel A) or placebo (panel B).

EXAMPLES

The following examples show the beneficial therapeutic effects on glycemic control and/or insulin resistance, etc., of using of SGLT2 inhibitors in equine animals, according to the present invention. These examples are intended to illustrate the invention in more detail without any limitation of the scope of the claims.

Example 1: Pharmacokinetics (PK)/Pharmacodynamics (PD) of Compound A Single Oral Dosing in Horses Compound A was administered to overnight fasted horses. The groups (n=3 per group) received a single oral or intravenous (i.v.) administration of either vehicle alone (purified water, macrogol 15 hydroxystearate) or vehicle containing the one or more SGLT2 inhibitors at a dose of 0.3 mg/kg bodyweight and 3 mg/kg bodyweight orally and 1 mg/kg bodyweight i.v. PK/PD measurements were taken until day 3 after a single administration of compound A or its vehicle.

TABLE 2

Pharmacokinetic data, single dose

| Parameter | | 1 mg/kg i.v. | 0.3 mg/kg p.o. | 3.0 mg/kg p.o. |
|---|---|---|---|---|
| $t_{max}$ [hour] | mean | | 2 | 1 |
| $C_{max}$ [nmol/L] | mean | | 353 | 3867 |
| $AUC_{0\rightarrow\infty}$ [nmol · h/l] | mean | 41251 | 2869 | 29752 |
| $T_{1/2}$ [hour] | mean | 7.9 | 8.5 | 8.2 |

Figure 1:
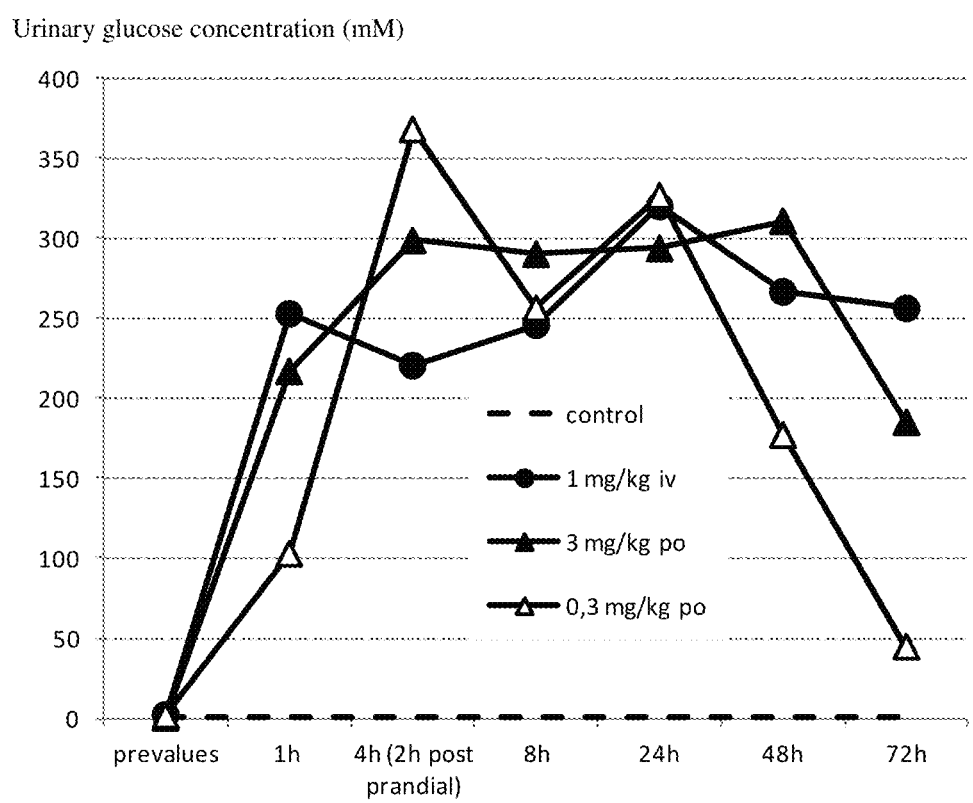
FIG. 1 shows that doses of 0.3 mg/kg bodyweight or 3 mg/kg bodyweight orally, or 1 mg/kg bodyweight i.v. of compound A, all caused prominent increases of urinary glucose concentration in horses.

Pharmacodynamic Data:

A prominent increase of urinary glucose concentration was evident at all doses already 1 hour after administration (mean group values: controls 0.6 mmol/L; 1 mg/kg i.v. −253 mmol/L; 0.3 mg/kg po—103 mmol/L; 3 mg/kg po—217 mmol/L) and was persistent for more than 24 hours (see FIG. 1).

None of the doses of compound A altered the basal blood glucose level in horses as compared to normal reference values.

None of the doses of compound A altered the renal function of horses.

Figure 2:
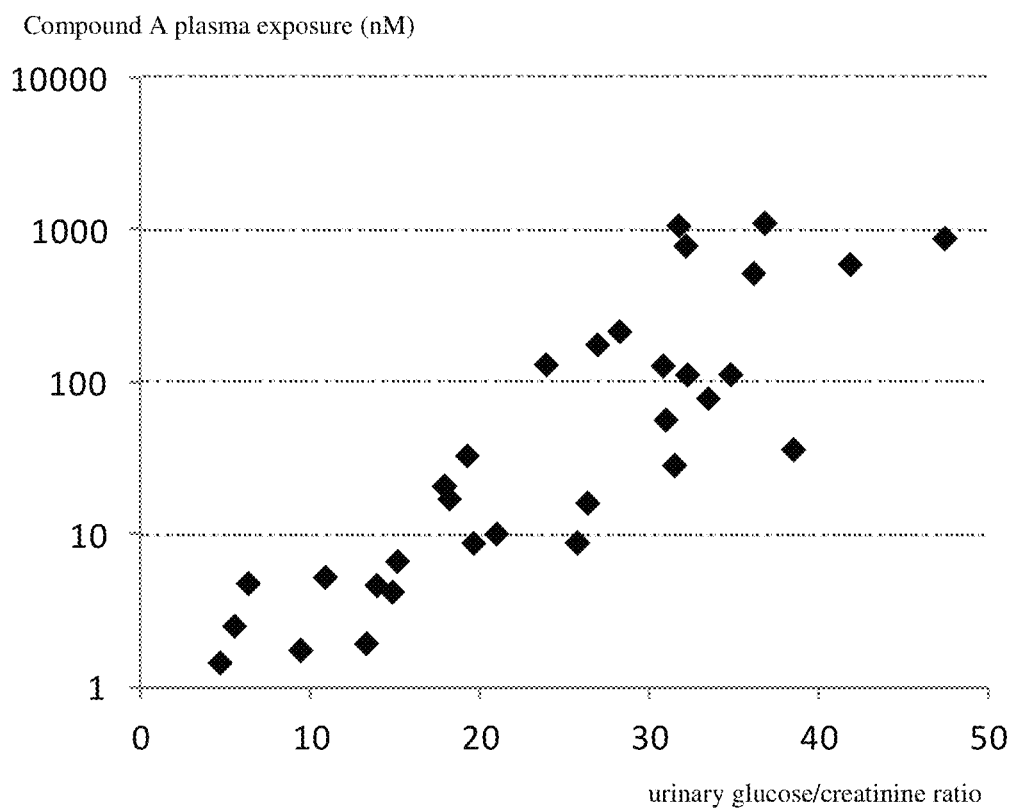
FIG. 2 shows the correlation between compound A plasma level and urinary glucose excretion normalized to urinary creatinine (glucose/creatinine).

Urinary glucose excretion increase is clearly plasma compound exposure dependent, as shown in FIG. 2.

Example 2. The Effect of Compound A on Urinary and Blood Glucose as Well as Glucose Tolerance after Repeated Dosing in Horses Compound A was administered to freely fed normoglycemic, hyperinsulinemic, insulin resistant, obese horses, which exhibit an impaired glucose tolerance. The groups (n=4 per group) received a once daily oral administration of either vehicle alone (purified water, macrogol 15 hydroxystearate −0.2 mL/100 kg and approximately 35 mL of apple sauce) or vehicle containing the one or more SGLT2 inhibitors in increasing doses up to 1 mg/kg bodyweight for 4 weeks. The treated horses received a daily dose of compound A at 0.1 mg/kg bodyweight for the first 7 days, followed by 0.2 mg/kg bodyweight, from day 20 the dose was increased to 1 mg/kg bodyweight. Urinary glucose and blood glucose were measured. Additionally, to evaluate the glucose tolerance, blood glucose was measured during an oral sugar test (OST, corn syrup 0.15 mL/kg) was performed. Blood was collected via jugular vein catheters. Blood samples were taken prior and at 60, 90, 120, 150, 180, and 210 min relative to sugar application.

The urinary glucose concentration was significantly elevated by the treatment—controls <1 mmol/L; treated—~300 mmol/L.

Basal blood glucose levels remained within normal ranges in all horses throughout the study. No hypoglycemia was observed.

Figure 3:
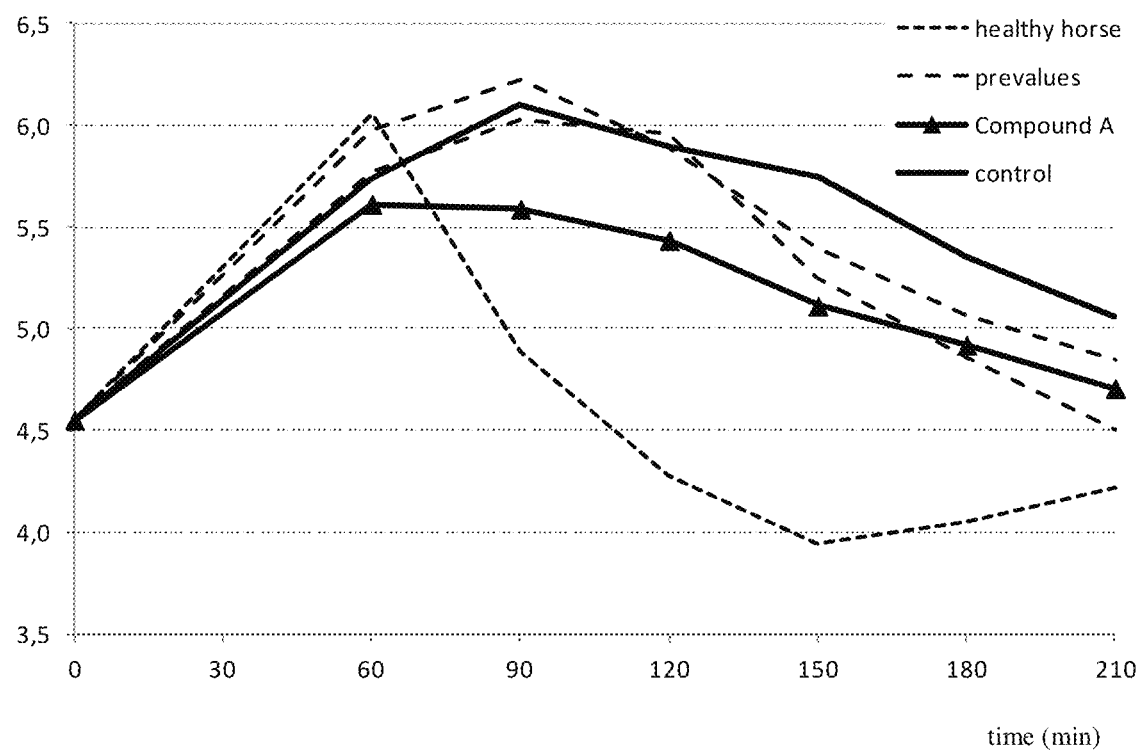
FIG. 3 compares relative changes in blood glucose over a period of 0-210 minutes (mean values; baseline as covariate) in an oral sugar test (OST) in treated and control animals on day 28 of the treatment period (bold lines) with the same animals on day −14 before the beginning of the treatment period (dotted lines). For comparison the fine dotted lines depicts the time course of the glucose excursion in the OST of a healthy glucose tolerant horse.

FIG. 3 shows blood glucose levels over a period of 0-210 minutes in an oral sugar test (OST) in animals treated with compound A and in control animals treated only with vehicle on day 28 of the treatment period. Mean values are shown (n=4 per group).

Comparison of the glucose curves at the end of the study revealed a statistically significant tendency (p=0.066) for a reduction of the glucose AUC in the horses treated with compound A. The plasma glucose concentration at 90 minutes after the challenge was significantly (p=0.038) lower in the treated horses.

These data indicate that treated horses experienced a significant improvement of their glucose tolerance.

Example 3. The Effect of Compound A on Postprandial Blood Glucose in Horses

Figure 4:
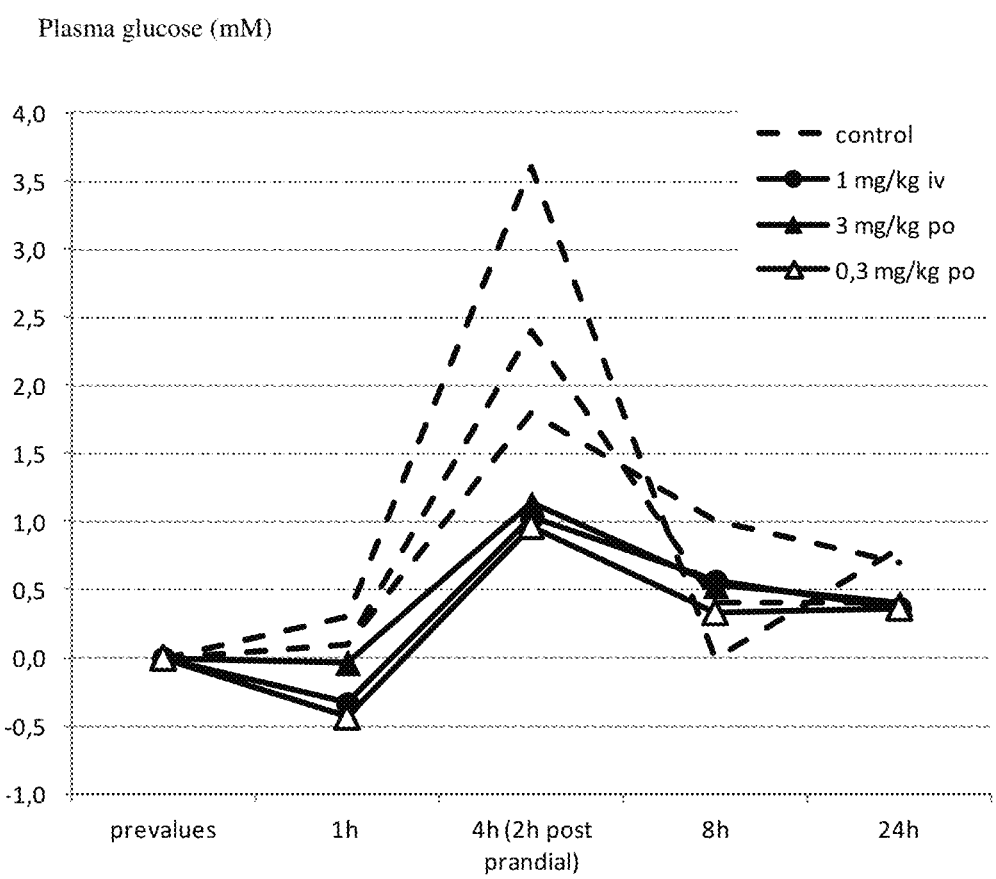
FIG. 4 shows the change of plasma glucose [mM] during a time courses after treatment with compound A or its vehicle and feeding. For the control group individual data are given, whereas for horses treated with compound A mean data are given for each dosing group (0.3 mg/kg bodyweight or 3 mg/kg bodyweight orally, or 1 mg/kg bodyweight i.v.).

The following example shows the effect of compound A on postprandial blood glucose in horses. Compound A was administered to overnight fasted horses. The groups (n=3 per group) received a single oral or i.v. administration of either vehicle alone (purified water, macrogol 15 hydroxystearate) or vehicle containing the one or more SGLT2 inhibitors at a dose of 0.3 mg/kg bodyweight and 3 mg/kg bodyweight orally and 1 mg/kg bodyweight i.v. Two hours after compound administration horses were fed a test meal. The postprandial glycaemia is quantified 2 hours thereafter and significantly blunted by all doses of compound A, as shown in FIG. 4. Compound A is thus clearly capable of effectively reducing postprandial glucose levels in horses.

The efficacy of SGLT2 inhibition in accordance with the invention in the treatment of pathological fasting glucose and/or insulin and/or impaired glucose tolerance can be tested using clinical studies. In studies over a shorter or longer period (e.g., 2-4 weeks or 1-2 years) the success of the treatment is examined by determining the fasting glucose and insulin values and/or the glucose values after a meal or after a loading test (oral glucose tolerance test or food tolerance test after a defined meal) after the end of the period of therapy for the study and comparing them with the values before the start of the study and/or with those of a placebo group. In addition, the fructosamine value can be determined before and after therapy and compared with the initial value and/or the placebo value. A significant drop in the fasting or non-fasting glucose and/or insulin and/or fructosamine levels demonstrates the efficacy of the treatment.

Example 4. Effect Upon Insulin Sensitivity and Plasma Insulin Levels in Horses

The following example shows the beneficial effect of compound A in insulin resistant obese horses. Compound A was administered to freely fed normoglycemic, obese horses. The groups (n=4 per group) received a once daily oral administration of either vehicle alone (purified water, macrogol 15 hydroxystearate –0.2 mL/100 kg and approximately 35 mL of apple sauce) or vehicle containing the one or more SGLT2 inhibitors in increasing doses up to 1 mg/kg bodyweight for 4 weeks. The following experiment was performed prior to treatment, and at the end of the 4 week treatment period. The treated horses received a daily dose of compound A at 0.1 mg/kg bodyweight for the first 7 days, followed by 0.2 mg/kg bodyweight, until day 20 from thereon until the end of the study the dose was increased to 1 mg/kg bodyweight. At days 28 and 30 the following experiment was performed twice, once approximately 2 h and another time approximately 24 h after the last administration of compound A or its vehicle.

An oral sugar test (OST, corn syrup 0.15 mL/kg) was performed. Blood was collected via jugular vein catheters. Blood samples were taken prior and at 60, 90, 120, 150, 180, and 210 min relative to sugar application. Glucose and insulin excursions were quantified by calculating the baseline corrected glucose AUC.

The significance of differences of means between groups was evaluated by repeated-measures two-factor (time & treatment) ANOVA and post hoc multiple comparisons versus control or the respective baseline readings.

Figure 5:
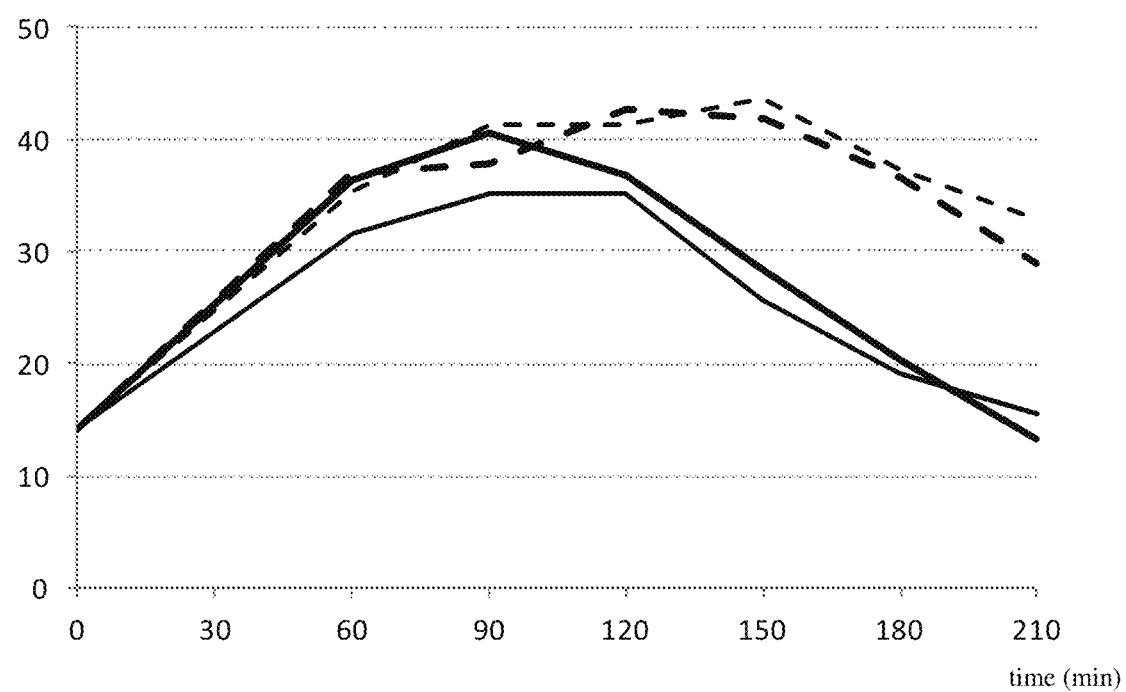
FIG. 5 shows a time course of blood insulin concentrations [μIU/mL] in insulin resistant horses during an OST after 4 weeks of treatment with compound A (solid lines) or its vehicle (dotted lines). Mean group values are given. Bold line: 2 hours after compound/vehicle administration; thinner line: 24 hours after last compound/vehicle administration.
Figure 8:
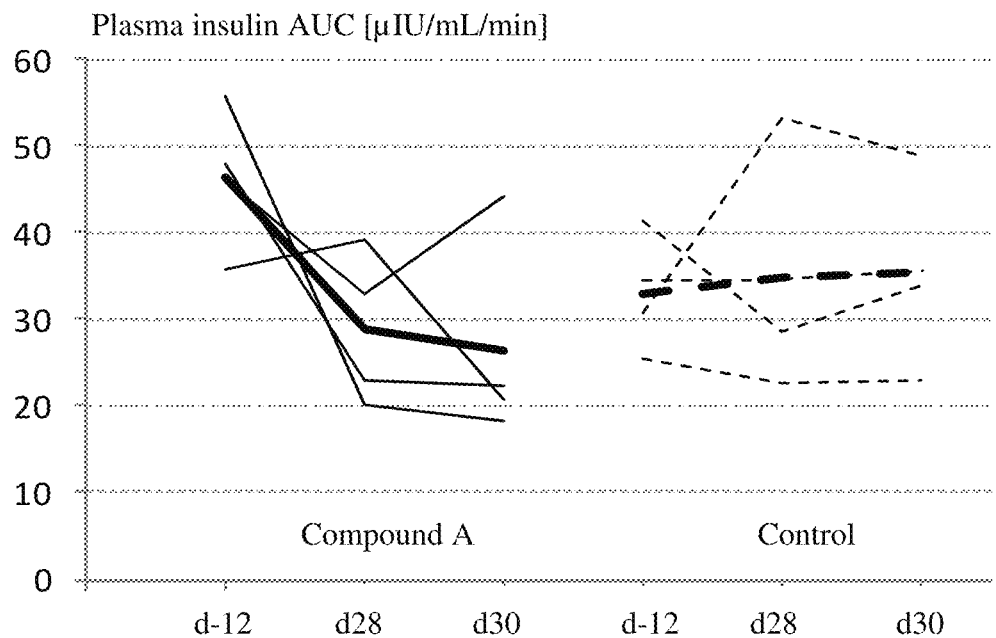
FIG. 8 shows plasma insulin AUC (area under curve) values [μIU/mL/min] (baseline as covariate) before treatment (day −12), on day 28 (2 hours after compound/vehicle administration) and on day 30 (24 hours after last compound/vehicle administration) of treatment with compound A or its vehicle. Individual data (thin lines) and the group mean values (bold lines) are given.

The baseline corrected glucose excursion during the OST did not change during the study period or by the treatment. The insulin excursion in control horses was not altered throughout the study period but was significantly reduced in treated horses as compared to pretreatment or control horses (p<0.05, see FIG. 8). FIG. 5 shows a time course of blood insulin concentrations [µIU/mL] in the insulin resistant obese horses during an OST after 4 weeks of treatment with compound A or its vehicle.

Figure 6:
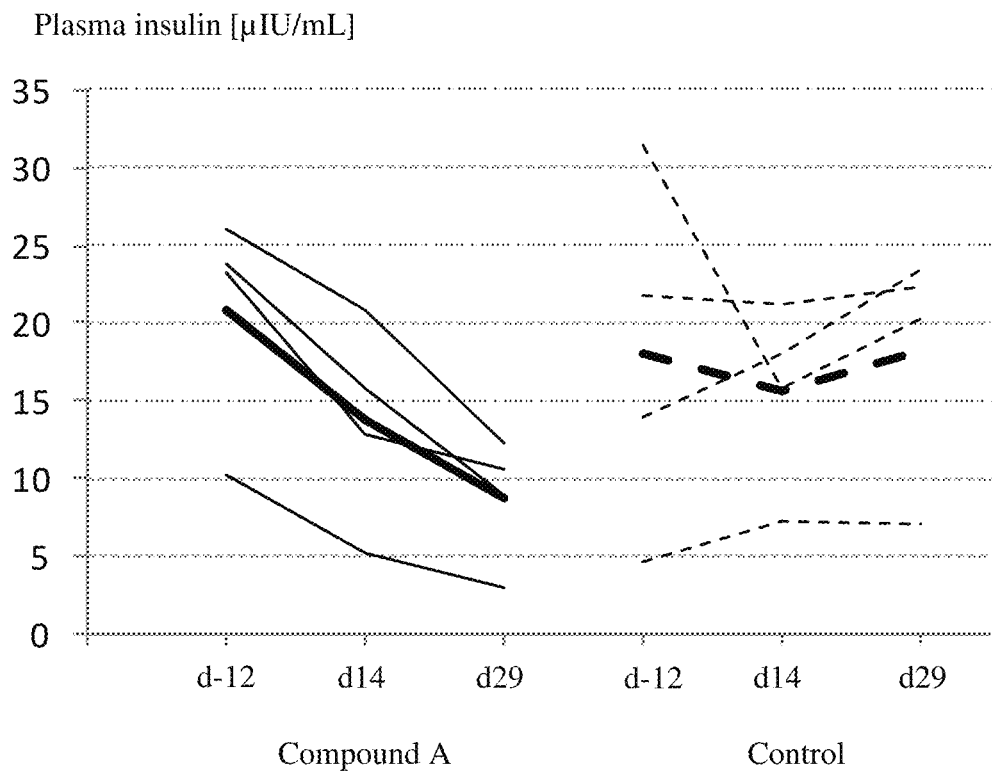
FIG. 6 shows basal plasma insulin levels [μIU/mL] before treatment (day −12), on day 14 and on day 29 of treatment with compound A or its vehicle. Individual data (thin lines) and the group mean values (bold lines) are given.

Plasma insulin levels significantly decreased over the four-week treatment period in horses treated with compound A, but remained essentially unchanged on average in control horses given vehicle only (see FIG. 6).

Figure 7:
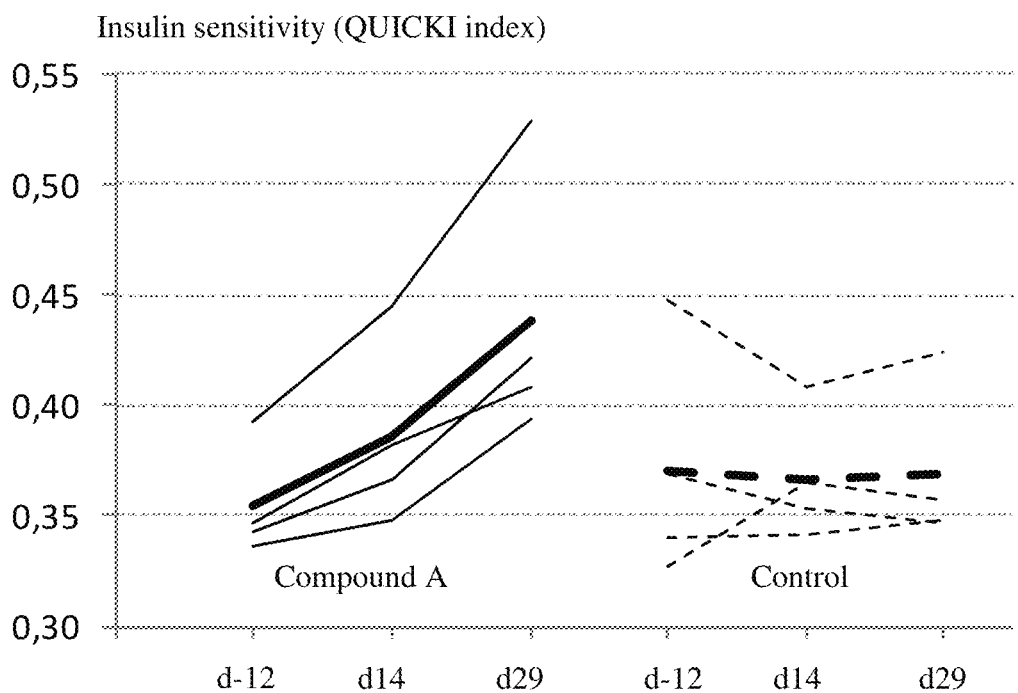
FIG. 7 shows the basal insulin sensitivity of treated and control horses as expressed by the QUICKI (quantitative insulin sensitivity check index, i.e., 1/(log(fasting insulin pmol/L)+log(fasting glucose mmol/L)). Measurements were taken before treatment (day −12), on day 14 and on day 29 of treatment with compound A or its vehicle. Individual data (thin lines) and the group mean values (bold lines) are given.
Figure 9:
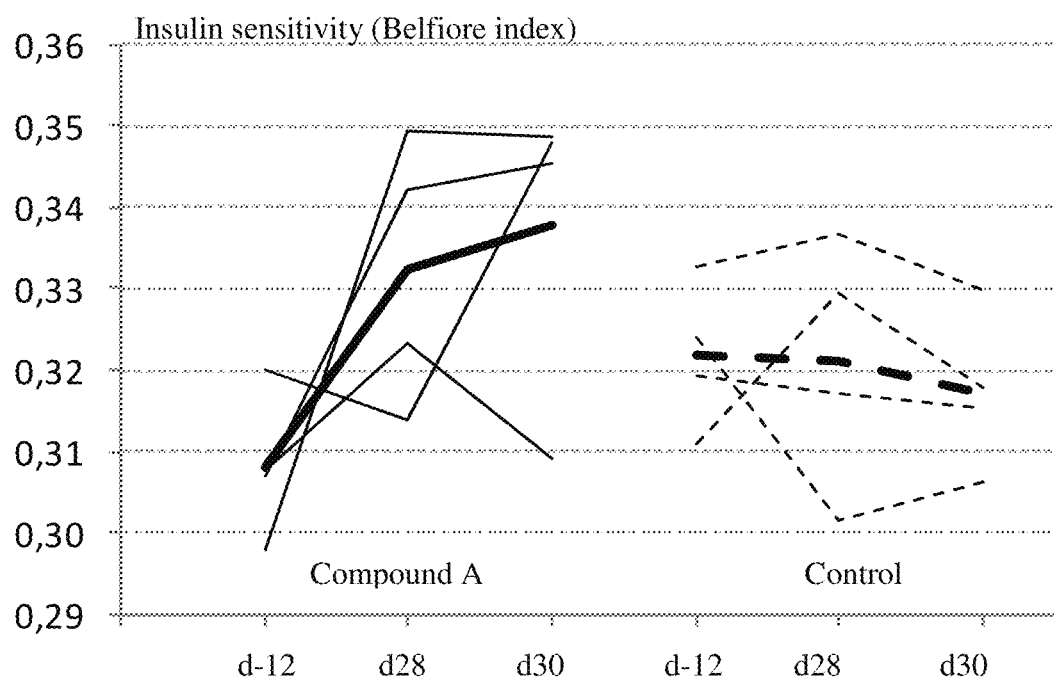
FIG. 9 shows the insulin sensitivity of treated and control horses as expressed by the Belfiore insulin sensitivity index (i.e., 1/(log(AUCΔinsulin×AUCΔ glucose)). Measurements were taken before treatment (day 12), on day 28 (2 hours after compound/vehicle administration) and on day 30 (24 hours after last compound/vehicle administration) of treatment with compound A or its vehicle. Individual data (thin lines) and the group mean values (bold lines) are given.

Insulin sensitivity was significantly increased in treated horses as compared to pretreatment values. This was demonstrated by determining basal insulin sensitivity values as expressed by the QUICKY index (1/log(gluc*ins) and during the challenge (OST) by the modified Belfiore index (1/log($\Delta$AUC gluc*$\Delta$AUC ins). As shown in FIG. 7 and in FIG. 9, in the course of the four-week treatment period, insulin sensitivity significantly increased in treated horses, but remained essentially unchanged in control horses given vehicle only.

These data indicate that the insulin resistance was significantly improved after a 2 to 4 week treatment with compound A.

Example 5. Effect Upon Dyslipidemia, Dysadipokinemia and Body Weight/Obesitas in Horses The following example shows the beneficial effect of compound A in insulin resistant obese horses. The details of the experiments are described in example 4.

Figure 10A:
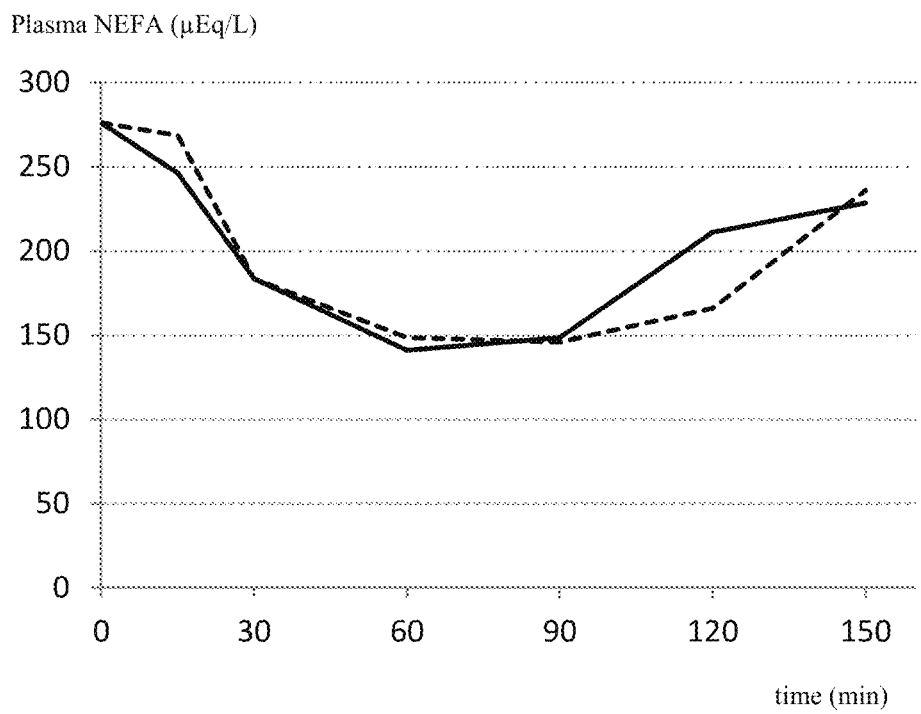
FIG. 10A shows the time course of the elimination of non-esterified fatty acids (NEFAs, µEq/L) from the bloodstream as measured during an intravenous insulin tolerance test (ivITT) prior to the treatment period. Mean group values are given of the horses treated with compound A (solid lines) or its vehicle (dotted lines).
Figure 10B:
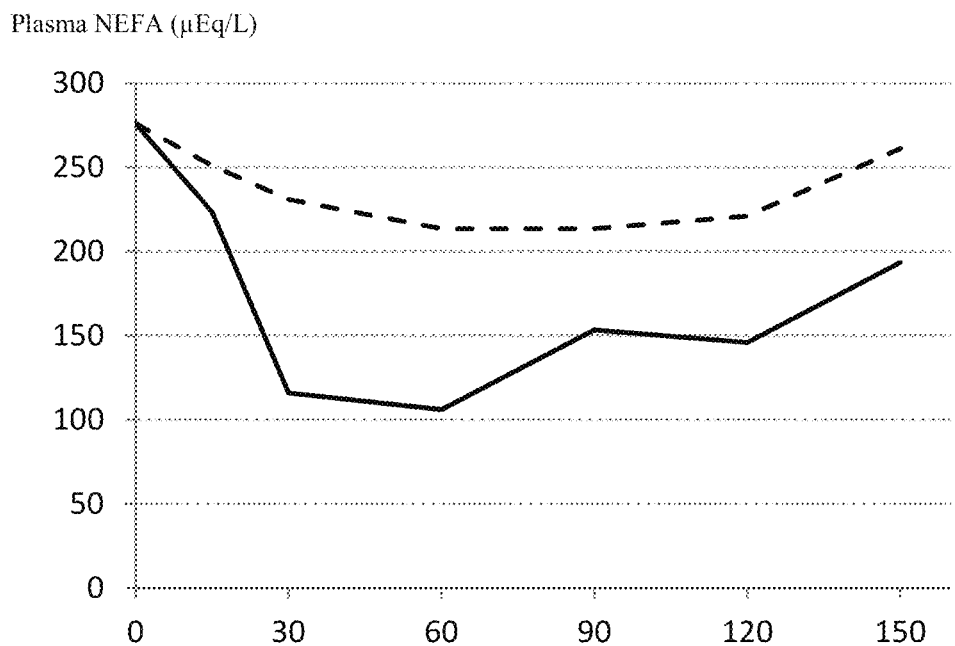
FIG. 10B shows the time course of the elimination of non-esterified fatty acids (NEFAs, µEq/L) from the bloodstream as measured during an intravenous insulin tolerance test (ivITT) and represent the results after 5 weeks of treatment. Mean group values are given of the horses treated with compound A (solid lines) or its vehicle (dotted lines).

To test the effect of compound A treatment on blood lipid handling/elimination, an intravenous insulin tolerance test (ivITT, 0.03 U insulin per kg body mass) was performed prior to start of and on day 35 of the treatment period. The test was performed prior to the morning feeding and approximately 24 hours after the last administration of compound A or its vehicle (day 35 only). Blood was collected prior to and at 15, 30, 60, 90, 120 and 150 minutes after the insulin challenge. FIG. 10 shows a time course of baseline corrected blood NEFA concentrations [µEq/L] in the insulin resistant obese horses during an ivITT.

The baseline corrected NEFA elimination curve during the ITT was clearly not different between the groups prior to treatment (see FIG. 10, panel A). At the end of the treatment period NEFA elimination was significantly improved by the compound A treatment (see FIG. 10, panel B).

Figure 11:
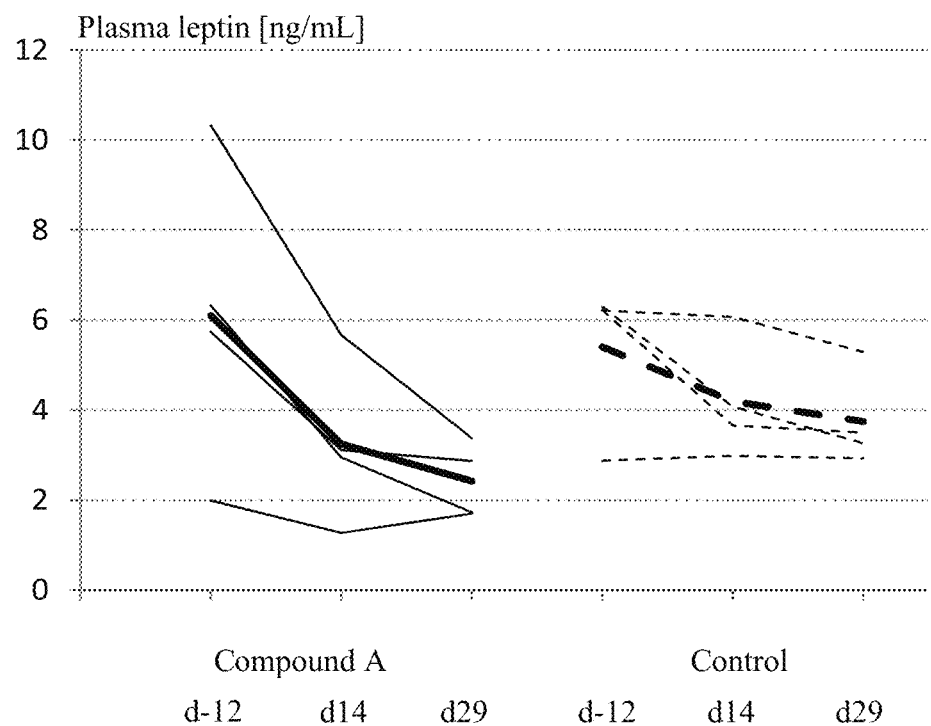
FIG. 11 shows the basal plasma leptin levels [ng/mL] before treatment (day −12), on day 14 and on day 29 of treatment with compound A or its vehicle. Individual data (thin lines) and the group mean values (bold lines) are given.

The use of one or more SGLT2 inhibitors according to the present invention advantageously also reduced blood leptin levels. As shown in FIG. 11, in the course of the four-week treatment period, plasma leptin concentrations significantly decreased in treated horses, but remained essentially unchanged in control horses given vehicle only.

Figure 12:
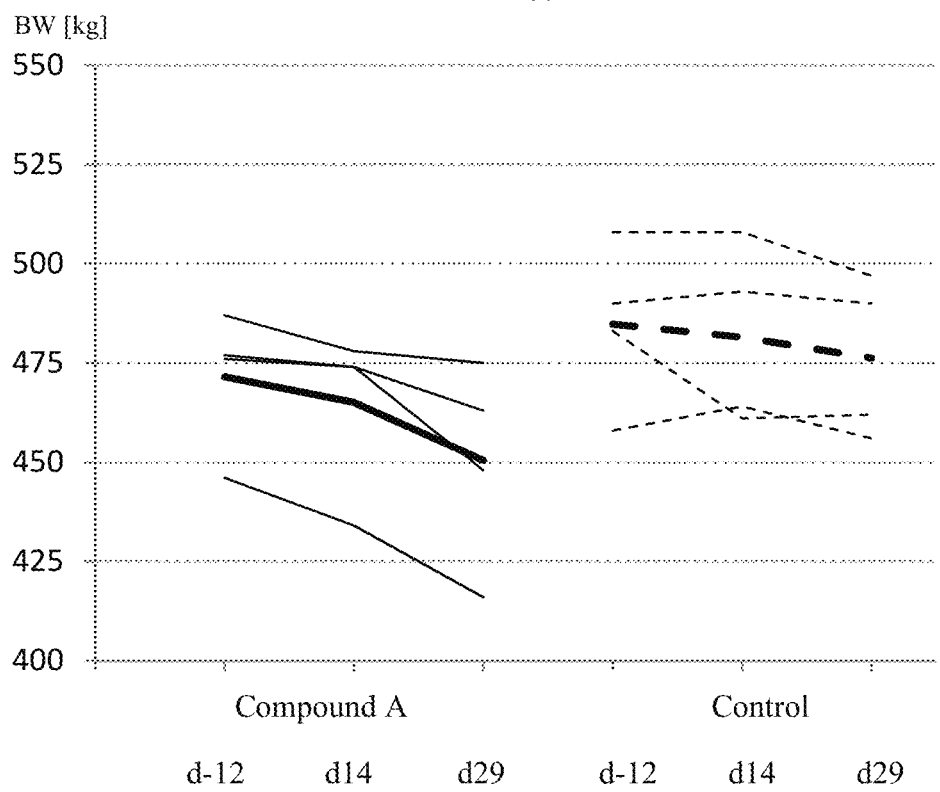
FIG. 12 shows the horses body mass [kg] before treatment (day −12), on day 14 and on day 29 of treatment with compound A or its vehicle. Individual data (thin lines) and the group mean values (bold lines) are given.

Additionally, the use of one or more SGLT2 inhibitors according to the present invention also reduced significantly the body weight of obese horses treated with compound A (see FIG. 12) in the course of the four-week treatment period.

These data indicate that after a 2 to 5 week treatment with compound A obese, insulin resistant horses showed significantly improved handling of blood lipids (elimination after a challenge) and an improved adipokine profile with reduced blood leptin concentrations. Additionally, the body weight was significantly reduced by treatment with compound A and indicates the potential to influence obesity and/or regional adiposity in horses.

The efficacy of SGLT2 inhibition in accordance with the invention in the treatment of pathological obesity and/or regional adiposity can be tested using clinical studies. In studies over a shorter or longer period (e.g., 3-6 months or 1-2 years) the success of the treatment is examined by determining e.g., body weight, body condition scores, other morphometric measurements or non-invasive body composition determination methods, e.g., ultrasound determination of fat pad dimension or deuterium oxide dilution (heavy water) methods. A significant difference in these values during or at the end of the study, compared with the initial value or compared with a placebo group, or a group given a different therapy, proves the efficacy of a pharmaceutical composition according to the invention in the reduction of obesitas and/or regional adipositas.

Example 6. Effects on Parameters of Inflammation

In studies in horses with metabolic disorders according to the present invention running for different lengths of time (e.g., 2 weeks to 12 months) the effect of the treatment with SGLT2 inhibitors according to the invention on inflammation (be it subclinical inflammation, systemic inflammation, low grade systemic inflammation) is evaluated by determining in the blood stream for example the concentration of proinflammatory cytokines (e.g., TNF-alpha or IL-6) or acute phase proteins (e.g., serum amyloid A or haptoglobulin). A significant fall in these values during or at the end of the study, compared with the initial value or compared with a placebo group, or a group given a different therapy, proves the efficacy of a pharmaceutical composition according to the invention in the reduction of parameters of inflammation in horses with metabolic disorders.

Example 7. Effects on Equine Metabolic Syndrome and Associated Diseases as Laminitis In studies in horses with metabolic disorders according to the present invention, particularly in studies in horses with equine metabolic syndrome and/or pituitary pars intermedia dysfunction and associated diseases as laminitis running for different lengths of time (e.g., 2 weeks to 12 months) e.g., the success of the improvement in insulin resistance can be checked using the measurement of baseline blood glucose, blood fructosamine and blood insulin level and there corresponding relation in the individual horse. Also the glucose and insulin values after a meal or after a loading test (glucose tolerance test or insulin tolerance test) after or during a period of therapy and comparing them with the values before the start of the study and/or with those of a placebo group can be employed. Additionally, the incidence of laminitis and/or the reduction of lameness and/or time to recovery from a laminitis episode can be evaluated with respect to the initial lameness values and the time course of lameness throughout an observation period.

Also the comparison with a placebo group or a group given a different therapy can prove the efficacy of a pharmaceutical composition according to the invention.

Example 8. Effects of Compound A on Insulin Resistance and Hyperinsulinemia in Horses Suffering from Equine Pituitary Pars Intermedia Dysfunction (PPID)

The following example shows the beneficial effect of compound A in an insulin resistant horse with PPID. PPID was diagnosed based on blood ACTH values—normal ACTH being below 30 pg/mL. The respective horse exhibited an ACTH blood concentration of 966 pg/mL, was thus clearly diagnosed to suffer from PPID.

An in-feed oral glucose challenge test was performed prior to treatment and at the end of a 4 week treatment period. For this test, oral dextrose powder at 1 g/kg bodyweight was dissolved in 100 ml tap water and added to 200 g to wheat bran plus lucerne chaff. Blood was collected via the jugular vein prior to the challenge and 2 hours thereafter.

The horse received a once daily dose of 0.3 mg/kg of compound A dissolved in purified water, macrogol 15 hydroxystearate. Compound A was given orally with some apple sauce for 4 weeks. Prior to the treatment there was a clear evidence of hyperinsulinemia, the basal plasma insulin concentrations were 19 µIU/mL. Treatment clearly decreased the basal hyperinsulinemia to normal concentrations (4 µIU/mL) and also clearly reduced the rise of insulin in response to the challenge by 45%. The blood glucose response was also slightly reduced—in consequence when determining the insulin sensitivity values as expressed by the QUICKY index (1/log(gluc*ins)) 4 weeks of treatment increased basal insulin sensitivity to 160% of the prevalue.

The data show that hyperinsulinemia and insulin resistance in horses with PPID can be significantly improved by treatment with SGLT2 inhibitors, e.g., compound A.

Example 9. Effects of Compound A in Horses with Metabolic Disorders and Associated Diseases as Laminitis In the following example horses were selected for a clinical study based on diagnosis of a metabolic disorder, i.e., hyperinsulinemia and/or insulin resistance. Insulin resistance was determined with an in-feed oral glucose challenge test, as described above in Example 8. Elected horses underwent a dietary challenge, i.e., the horses were fed a diet containing non-structural carbohydrates (NSC) from oats and molasses at an amount of 10-12 g NSC per kg body weight of the horse. The dietary challenge was stopped at onset of laminitis and the horses were examined for lameness at days 10 and 2 and 4 weeks after onset. Clinical or subclinical laminitis was diagnosed by a score system including evaluation of weight shifting, response to foot lift, gait at the walk and trot and in circle, as well as response to a hoof tester. The dietary challenge induced laminitis in around 90% of horses, i.e., out of 8 treatment naive horses 4 developed clinical laminitis and 3 subclinical laminitis.

Two horses that were very comparable in their insulin resistance and showed a similar degree of laminitis (score 3.5 and 4, respectively) were at onset of laminitis randomly assigned to treatment with compound A or placebo. Compound A or placebo was given with some apple sauce once daily orally at a dose of 0.3 mg/kg of compound A dissolved in purified water, macrogol 15 hydroxystearate. In the horse that was treated with compound A, the laminitis was resolved already at day 10. In contrast, the horse receiving placebo still had a lameness score of 1 on day 10 and 2 weeks after onset of laminitis, only at the 4 week examination the horse was fully lameness free.

Additionally, in-feed oral glucose challenge tests to determine the effects on insulin resistance were performed. FIG. 15 shows the change in blood glucose and insulin levels in response to the glucose challenge before the dietary challenge and at day 14 after onset of laminitis. The treatment with compound A clearly reduced the rise of insulin in response to the challenge by 88% as compared to prevalue.

This parallels with the observation that the treated horse was already free of lameness at this point, whereas the horse receiving placebo was still scored to be clinically abnormal.

Figure 16A:
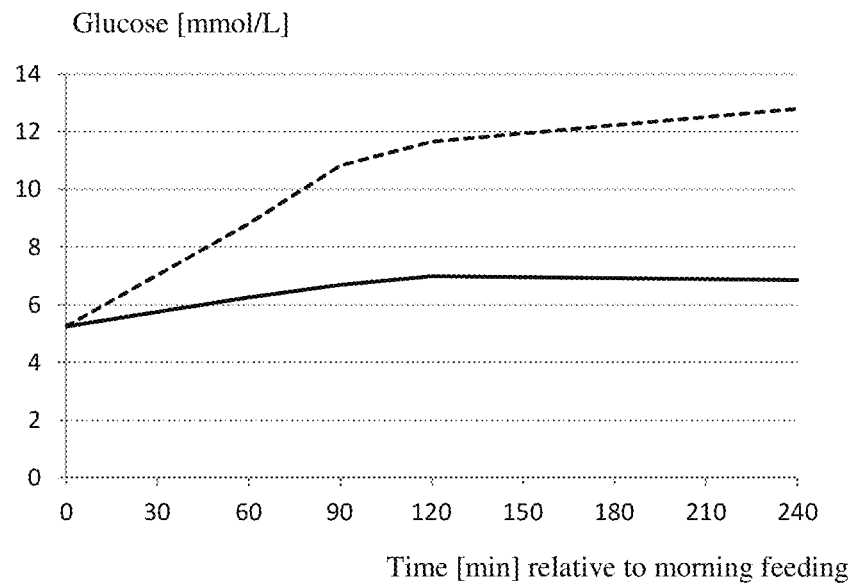
FIG. 16A shows relative changes (group mean values; baseline as covariate) of blood glucose over a period of 0-240 minutes relative to the morning feeding on day 2 of the dietary challenge. Bold lines: horses treated with compound A (n=3), dotted lines: untreated controls (n=8).
Figure 16B:
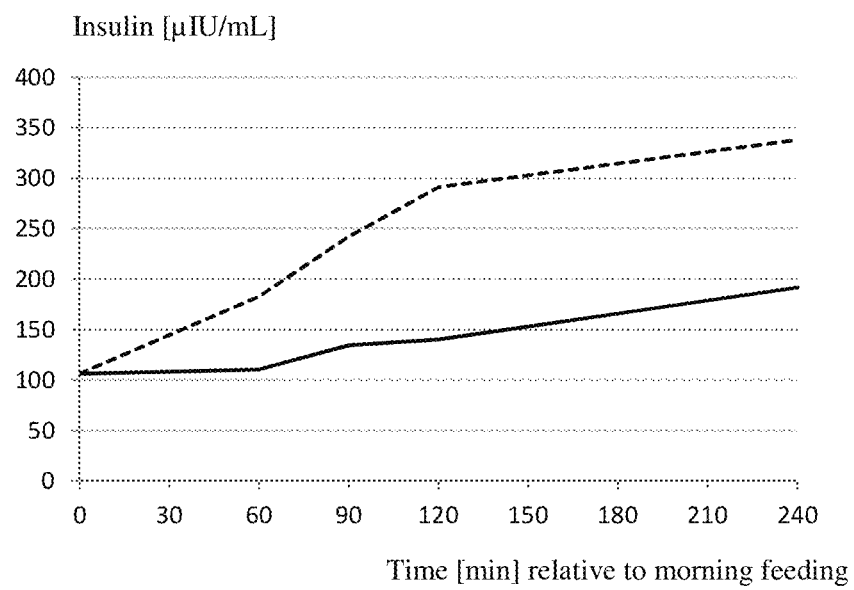
FIG. 16B shows relative changes (group mean values; baseline as covariate) of insulin levels over a period of 0-240 minutes relative to the morning feeding on day 2 of the dietary challenge. Bold lines: horses treated with compound A (n=3), dotted lines: untreated controls (n=8).

A different set of insulin resistant horses (n=3) were treated with compound A for 3 weeks prior to the start and throughout the dietary challenge as described above. Compound A was given with some apple sauce once daily orally at a dose of 0.3 mg/kg of compound A dissolved in purified water, macrogol 15 hydroxystearate. In untreated horses with insulin resistance the dietary challenge induced a strong and long lasting increase of blood glucose and insulin. FIG. 16 shows the time course of blood glucose and insulin levels over a period of 0-240 minutes relative to the morning feeding on day 2 of the dietary challenge. The horses pretreated with compound A clearly profited from the treatment in that their glucose and insulin excursions were significantly decreased as compared to untreated horses (n=8) (glucose p=0.003; insulin p=0.06). This is also reflected when calculating the insulin sensitivity as determined in with the relative area under curve by the modified Belfiore index (1/log(ΔAUC gluc*ΔAUC ins). This was significantly increased by the treatment with compound A (p=0.01) as compared to the untreated horses. Basal insulin levels were also reduced by the treatment with Compound A (mean 51 µIU/mL) as compared to untreated horses. Basal insulin levels were also reduced by the treatment with Compound A (mean 51 µIU/mL) as compared to untreated horses (mean 140 µIU/mL), though these values did not reach statistical significance due to low numbers and variability of the data. Thus, a clear beneficial effect of treatment with compound A on glycemic control and insulin resistance could be observed and this parallels with the observation, that in this subset of horses by day 13 of the dietary challenge none had developed clinical laminitis.

The data clearly indicate that in horses with metabolic disorders according to the present invention, particularly in studies in horses with insulin resistance associated with equine metabolic syndrome and/or pituitary pars intermedia dysfunction which is associated with clinical signs as laminitis the treatment with SGLT2 inhibitors, e.g., compound A, can improve not only the insulin resistance, but also reduce the time to recovery from a laminitis episode as well as prevent the development of laminitis.

Example 10. Preparation of 1-cyano-2-(4-cyclopropyl-benzyl)-4-(β-D-glucopyranos-1-yl)-benzene (Compound A)

In the foregoing and following text, H atoms of hydroxyl groups are not explicitly shown in every case in structural formulae. The following example of synthesis serves to illustrate a method of preparing 1-cyano-2-(4-cyclopropyl-benzyl)-4-(β-D-glucopyranos-1-yl)-benzene (compound A). A method of preparing its crystalline complex with L-proline is also described. It is to be regarded only as a possible method described by way of example, without restriction of the scope of the invention. The terms "room temperature" and "ambient temperature" are used interchangeably and denote temperatures of about 20° C. The following abbreviations are used:

DMF dimethylformamide
NMP N-methyl-2-pyrrolidone
THF tetrahydrofuran

Preparation of 4-bromo-3-hydroxymethyl-1-iodo-benzene

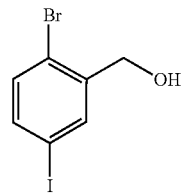

Oxalyl chloride (13.0 mL) is added to an ice-cold solution of 2-bromo-5-iodo-benzoic acid (49.5 g) in $CH_2Cl_2$ (200 mL). DMF (0.2 mL) is added and the solution is stirred at room temperature for 6 hours. Then, the solution is concentrated under reduced pressure and the residue is dissolved in THF (100 mL). The resulting solution is cooled in an ice-bath and $LiBH_4$ (3.4 g) is added in portions. The cooling bath is removed and the mixture is stirred at room temperature for 1 hour. The reaction mixture is diluted with THF and treated with 0.1 M hydrochloric acid. Then, the organic layer is separated and the aqueous layer is extracted with ethyl acetate. The combined organic layers are dried ($Na_2SO_4$) and the solvent is evaporated under reduced pressure to give the crude product.

Yield: 47.0 g (99% of theory)

Preparation of 4-bromo-3-chloromethyl-1-iodo-benzene

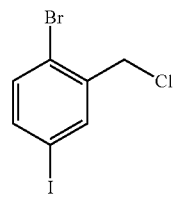

Thionyl chloride (13 mL) is added to a suspension of 4-bromo-3-hydroxymethyl-1-iodo-benzene (47.0 g) in dichloromethane (100 mL) containing DMF (0.1 mL). The mixture is stirred at ambient temperature for 3 hours. Then, the solvent and the excess reagent are removed under reduced pressure. The residue is triturated with methanol and dried.

Yield: 41.0 g (82% of theory)

Preparation of 4-bromo-1-iodo-3-phenoxymethyl-benzene

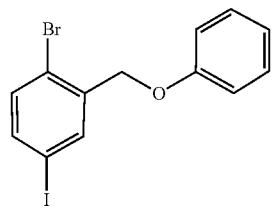 [SMILES: Brc1ccc(I)cc1COC1=CCC=CC=C1]

Phenol (13 g) dissolved in 4 M KOH solution (60 mL) is added to 4-bromo-3-chloromethyl-1-iodo-benzene (41.0 g) dissolved in acetone (50 mL). NaI (0.5 g) is added and the resulting mixture is stirred at 50° C. overnight. Then, water is added and the resulting mixture is extracted with ethyl acetate. The combined extracts are dried (Na$_2$SO$_4$) and the solvent is evaporated under reduced pressure. The residue is purified by chromatography on silica gel (cyclohexane/ethyl acetate 19:1).

Yield: 38.0 g (79% of theory)

Preparation of 1-bromo-4-(1-methoxy-D-glucopyranos-1-yl)-2-(phenoxymethyl)-benzene

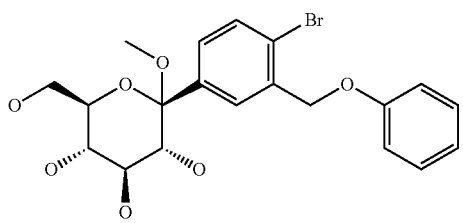 [SMILES: CO[C@@]1(c2ccc(Br)c(COc3ccccc3)c2)O[C@H](CO)[C@@H](O)[C@H](O)[C@H]1O]

A 2 M solution of iPrMgCl in THF (11 mL) is added to dry LiCl (0.47 g) suspended in THF (11 mL). The mixture is stirred at room temperature until all the LiCl is dissolved. This solution is added dropwise to a solution of 4-bromo-1-iodo-3-phenoxymethyl-benzene (8.0 g) in tetrahydrofuran (40 mL) cooled to –60° C. under argon atmosphere. The solution is warmed to –40° C. and then 2,3,4,6-tetrakis-O-(trimethylsilyl)-D-glucopyranone (10.7 g, 90% pure) in tetrahydrofuran (5 mL) is added. The resulting solution is warmed to –5° C. in the cooling bath and stirred for another 30 min at this temperature. Aqueous NH$_4$Cl solution is added and the resultant mixture is extracted with ethyl acetate. The combined organic extracts are dried over sodium sulfate and the solvent is removed under reduced pressure. The residue is dissolved in methanol (80 mL) and treated with methane sulfonic acid (0.6 mL) to produce the more stable anomer solely. After stirring the reaction solution at 35-40° C. overnight, the solution is neutralized with solid NaHCO$_3$ and the methanol is removed under reduced pressure. The remainder is diluted with aqueous NaHCO$_3$ solution and the resulting mixture is extracted with ethyl acetate. The combined extracts are dried over sodium sulfate and the solvent is evaporated to yield the crude product that is submitted to reduction without further purification.

Yield: 7.8 g (93% of theory)

Preparation of 1-bromo-4-(2,3,4,6-tetra-O-acetyl-D-glucopyranos-1-yl)-2-(phenoxymethyl)-benzene

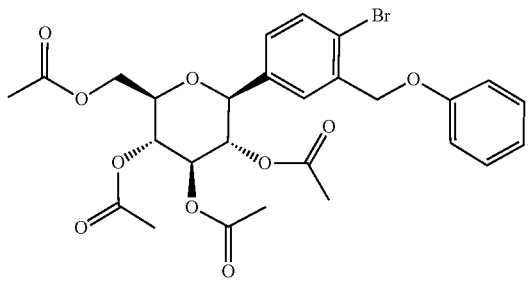 [SMILES: CC(=O)OC[C@H]1O[C@@H](c2ccc(Br)c(COc3ccccc3)c2)[C@H](OC(C)=O)[C@@H](OC(C)=O)[C@@H]1OC(C)=O]

Boron trifluoride diethyletherate (4.9 mL) is added to a solution of 1-bromo-4-(1-methoxy-D-glucopyranos-1-yl)-2-(phenoxymethyl)-benzene (8.7 g) and triethylsilane (9.1 mL) in dichloromethane (35 mL) and acetonitrile (50 mL) cooled to –20° C. at such a rate that the temperature maintains below –10° C. The resultant solution is warmed to 0° C. over a period of 1.5 hours and then treated with aqueous sodium hydrogen carbonate solution. The resulting mixture is stirred for 0.5 hours, the organic solvent is removed and the residue is extracted with ethyl acetate. The combined organic layers are dried over sodium sulfate and the solvent is removed. The residue is taken up in dichloromethane (50 mL) and pyridine (9.4 mL), acetic anhydride (9.3 mL) and 4-dimethylaminopyridine (0.5 g) are added in succession to the solution. The solution is stirred for 1.5 hours at ambient temperature and then diluted with dichloromethane. This solution is washed twice with 1 M hydrochloric acid and dried over sodium sulfate. After the solvent is removed, the residue is recrystallized from ethanol to furnish the product as a colorless solid.

Yield: 6.78 g (60% of theory)

Mass spectrum (ESI$^+$): m/z=610/612 (Br) [M+NH$_4$]$^+$

Preparation of 2-(phenoxymethyl)-4-(2,3,4,6-tetra-O-acetyl-D-glucopyranos-1-yl)-benzonitrile

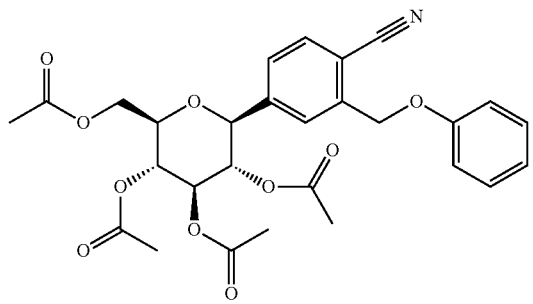 [SMILES: CC(=O)OC[C@H]1O[C@@H](c2ccc(C#N)c(COc3ccccc3)c2)[C@H](OC(C)=O)[C@@H](OC(C)=O)[C@@H]1OC(C)=O]

A flask charged with zinc cyanide (1.0 g), zinc (30 mg), Pd$_2$(dibenzylideneacetone)$_3$*CHCl$_3$ (141 mg) and tri-tert-butylphosphonium tetrafluoroborate (111 mg) is flushed with argon. Then a solution of 1-bromo-4-(2,3,4,6-tetra-O-acetyl-D-glucopyranos-1-yl)-2-(phenoxymethyl)-benzene (5.4 g) in NMP (12 mL) is added and the resulting mixture is stirred at room temperature for 18 hours. After dilution with ethyl acetate, the mixture is filtered and the filtrate is washed with aqueous sodium hydrogen carbonate solution. The organic phase is dried (sodium sulfate) and the solvent is removed. The residue is recrystallized from ethanol.

Yield: 4.10 g (84% of theory)

Mass spectrum (ESI$^+$): m/z=557 [M+NH$_4$]$^+$

Alternatively, the compound described above is synthesized starting from 1-bromo-4-(2,3,4,6-tetra-O-acetyl-D-glucopyranos-1-yl)-2-(phenoxymethyl)-benzene using copper(I) cyanide (2 equivalents) in NMP at 210° C.

Preparation of 2-bromomethyl-4-(2,3,4,6-tetra-O-acetyl-D-glucopyranos-1-yl)-benzonitrile

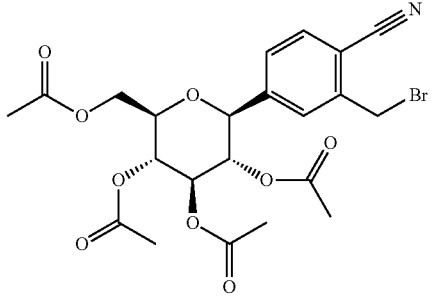 [SMILES: CC(=O)OC[C@H]1O[C@@H](c2ccc(C#N)c(CBr)c2)[C@H](OC(C)=O)[C@@H](OC(C)=O)[C@@H]1OC(C)=O]

A 33% solution of hydrobromic acid in acetic acid (15 mL) is added to a solution of 2-phenyloxymethyl-4-(2,3,4,6-tetra-O-acetyl-D-glucopyranos-1-yl)-benzonitrile (0.71 g) and acetic anhydride (0.12 mL) in acetic acid (10 ml). The resulting solution is stirred at 55° C. for 6 hours and then cooled in an ice-bath. The reaction mixture is neutralized with chilled aqueous potassium carbonate solution, and the resultant mixture is extracted with ethyl acetate. The combined organic extracts are dried over sodium sulfate and the solvent is removed under reduced pressure. The residue is taken up in ethyl acetate/cyclohexane (1:5), and the precipitate is separated by filtration and dried at 50° C. to give the pure product.

Yield: 0.52 g (75% of theory)

Mass spectrum (ESI$^+$): m/z=543/545 (Br) [M+NH$_4$]$^+$

Preparation of 4-cyclopropyl-phenylboronic Acid

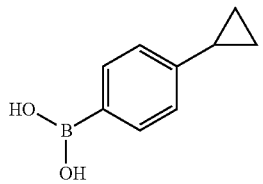 [SMILES: OB(O)c1ccc(C2CC2)cc1]

2.5 M solution of nButyllithium in hexane (14.5 mL) is added dropwise to 1-bromo-4-cyclopropyl-benzene (5.92 g) dissolved in THF (14 mL) and toluene (50 mL) and chilled to −70° C. The resultant solution is stirred at −70° C. for 30 min before triisopropyl borate (8.5 mL) is added. The solution is warmed to −20° C. and then treated with 4 M aqueous hydrochloric acid (15.5 mL). The reaction mixture is further warmed to room temperature and then the organic phase is separated. The aqueous phase is extracted with ethyl acetate and the combined organic phases are dried (sodium sulfate). The solvent is evaporated and the residue is washed with a mixture of ether and cyclohexane to give the product as a colorless solid.

Yield: 2.92 g (60% of theory)

Mass spectrum (ESI$^-$): m/z=207 (Cl) [M+HCOO]$^-$

Preparation of 1-cyano-2-(4-cyclopropyl-benzyl)-4-(β-D-glucopyranos-1-yl)-benzene

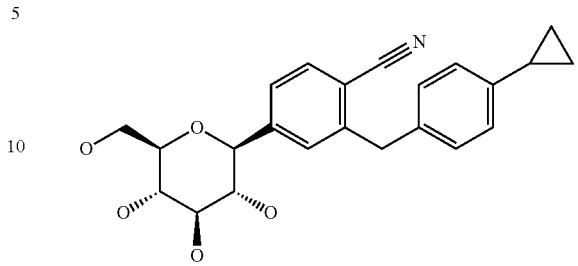

An Argon filled flask is charged with 2-bromomethyl-4-(2,3,4,6-tetra-O-acetyl-D-glucopyranos-1-yl)-benzonitrile (1.60 g), 4-cyclopropyl-phenylboronic acid (1.0 g), potassium carbonate (1.85 g) and a degassed 3:1 mixture of acetone and water (22 mL). The mixture is stirred at room temperature for 5 min, before it is cooled in an ice-bath. Then palladium dichloride (30 mg) is added and the reaction mixture is stirred for 16 hours at ambient temperature. The mixture is then diluted with brine and extracted with ethyl acetate. The combined extracts are dried over sodium sulfate and the solvent is removed under reduced pressure. The residue is dissolved in methanol (20 mL) and treated with 4 M aqueous potassium hydroxide solution (4 mL). The resulting solution is stirred at ambient temperature for 1 hour and then neutralized with 1 M hydrochloric acid. The methanol is evaporated, and the residue is diluted with brine and extracted with ethyl acetate. The organic extracts collected are dried over sodium sulfate, and the solvent is removed. The residue is chromatographed on silica gel (dichloromethane/methanol 1:0→8:1).

Yield: 0.91 g (76% of theory)

Mass spectrum (ESI$^+$): m/z=413 [M+NH$_4$]$^+$

Preparation of a Crystalline Complex (1:1) of Compound A with L-Proline

L-proline (0.34 g) dissolved in 2.1 mL of a mixture of ethanol and water (volume ratio 10:1) is added to a solution of 1-cyano-2-(4-cyclopropyl-benzyl)-4-(β-D-glucopyranos-1-yl)-benzene (1.17 g, obtained as described above) dissolved in 2 mL ethanol. The resulting solution is allowed to stand at ambient temperature. After about 16 hours, the crystalline complex is isolated as white crystals by filtration. If necessary the crystallization may be initiated by scratching with a glass rod or metal spatula for example, or by inoculating with seed crystals. Residual solvent is removed by storing the crystals at slightly elevated temperature (30 to 50° C.) under vacuum for about 4 hours to yield 1.27 g of the crystalline 1:1 complex of L-proline and 1-cyano-2-(4-cyclopropyl-benzyl)-4-(β-D-glucopyranos-1-yl)-benzene.

Figure 13:
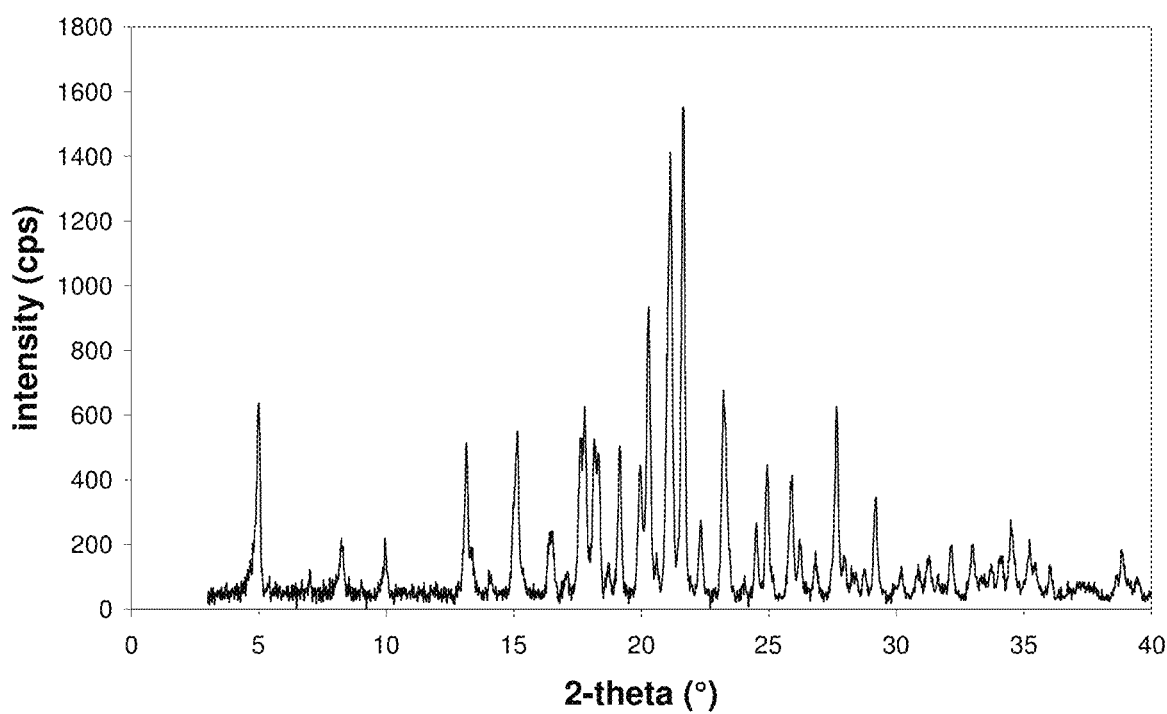
FIG. 13 shows an X-ray powder diffraction pattern of a representative batch of a crystalline complex of compound A with L-proline (1:1).
Figure 14:
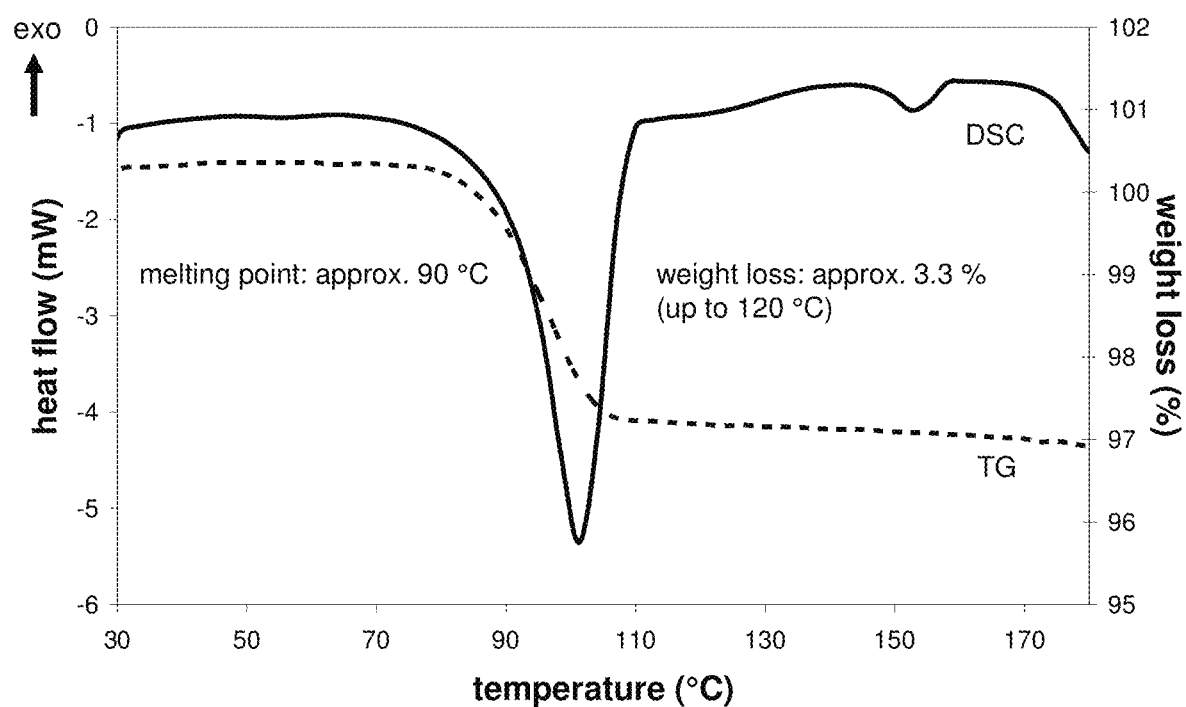
FIG. 14 shows a DSC/TG diagram of a representative batch of a crystalline complex of compound A with L-proline (1:1).

Several batches of the crystalline complex according to the above preparation are obtained. The X-ray powder diffraction patterns coincide. The melting points were determined via DSC and evaluated as onset-temperature. Examples of melting points are approximately 89° C., 90° C., 92° C., 101° C. and 110° C. The X-ray powder diffraction pattern as contained in Table 2 and as depicted in FIG. 13 the DSC and TG diagram in FIG. 14 correspond to a batch with a melting point of approximately 90° C.

The X-ray powder diffraction pattern of the crystalline complex of the compound A and L-proline (peaks up to 30° in 2 Θ) is provided above in Table 1.

Example 11. Formulations

Some examples of formulations are described in which the term "active substance" denotes one or more SGLT2 inhibitors or pharmaceutically acceptable forms thereof, e.g., a prodrug or a crystalline form, for use according to the invention. In the case of a combination with one or additional active substances, the term "active substance" may also include the additional active substance.

Tablets Containing 100 mg of Active Substance
Composition:
1 tablet contains:

| active substance | 100.0 mg |
|---|---|
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type dryer at 50° C. it is screened again (1.5 mm mesh size) and the lubricant is added. The finished mixture is compressed to form tablets.

Weight of tablet: 220 mg
Diameter: 10 mm, biplanar, faceted on both sides and notched on one side.

Tablets Containing 150 mg of Active Substance
Composition:
1 tablet contains:

| active substance | 150.0 mg |
|---|---|
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

Hard Gelatin Capsules Containing 150 mg of Active Substance
Composition:
1 capsule contains:

| active substance | 150.0 mg |
|---|---|
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatin capsules.

Capsule filling: approx. 320 mg
Capsule shell: size 1 hard gelatin capsule.

Suppositories Containing 150 mg of Active Substance
Composition:
1 suppository contains:

| active substance | 150.0 mg |
|---|---|
| polyethylene glycol 1500 | 550.0 mg |
| polyethylene glycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled molds.

Ampoules Containing 10 mg Active Substance
Composition:

| active substance | 10.0 mg |
|---|---|
| 0.01N hydrochloric acid/NaCl | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

Ampoules Containing 50 mg of Active Substance
Composition:

| active substance | 50.0 mg |
|---|---|
| 0.01N hydrochloric acid/NaCl | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

REFERENCES

All references cited herein are incorporated by reference in their entirety.

1) Katz & Bailey (2012) Equine Veterinary Journal 44:752-761
2) Venugopal et al. (2011) Equine Veterinary Journal 43:744-749
3) Treiber et al. (2006) The Journal of Nutrition 136 (7 Suppl):2094S-2098S
4) Tinworth et al. (2012) The Veterinary Journal 191:79-84
5) Gehlen (2014) Journal of Equine Veterinary Science 34(4): 508-513
6) Frank et al. (2011) Journal of Veterinary Internal Medicine 24(3):467-75
7) WO01/27128
8) WO03/099836
9) WO2005/092877
10) WO2006/034489
11) WO2006/064033
12) WO2006/117359

13) WO2006/117360
14) WO2007/025943
15) WO2007/028814
16) WO2007/031548
17) WO2007/093610
18) WO2007/128749
19) WO2008/049923
20) WO2008/055870
21) WO2008/055940
22) WO2009/022020
23) WO2009/022008
24) WO2008/116179
25) WO2008/002824
26) WO2005/012326
27) WO2009/035969
28) WO2008/069327
29) WO2006/120208
30) WO2011/039108
31) WO2011/039107
32) WO2004/007517
33) WO2004/080990
34) WO2007/114475
35) WO2007/140191
36) WO2008/013280
37) WO2010/023594
38) EP1213296
39) EP1354888
40) EP1344780
41) EP1489089
42) WO2008/042688
43) WO2009/014970
44) WO2014/016381

The invention claimed is:

1. A method of treating or preventing a metabolic disorder in an equine comprising administering an SGLT2 inhibitor or pharmaceutically acceptable form thereof, wherein said SGLT2 inhibitor or pharmaceutically acceptable form thereof consists of 1-cyano-2-(4-cyclopropyl-benzyl)-4-(β-D-glucopyranos-1-yl)-benzene, represented by the following formula:

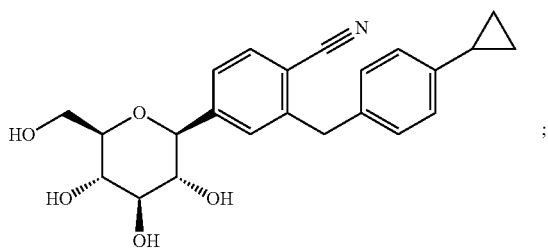 [SMILES: N#Cc1ccc([C@@H]2O[C@H](CO)[C@@H](O)[C@H](O)[C@H]2O)cc1Cc1ccc(C2CC2)cc1]

wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome.

2. The method according to claim 1, wherein the metabolic disorder is a clinical condition or sign associated with insulin resistance or hyperinsulinaemia.

3. The method according to claim 1, wherein the metabolic disorder is hyperinsulinemia and/or insulin resistance, and wherein said hyperinsulinemia and/or insulin resistance is associated with one or more of laminitis, vascular dysfunction, hypertension, hepatic lipidosis, atherosclerosis, hyperadrenocorticism, Pituitary Pars Intermedia Dysfunction and/or Equine Metabolic Syndrome.

4. The method according to claim 1, wherein the equine animal is a horse or a pony.

5. The method according to claim 1, wherein the equine animal is obese and/or exhibits regional adiposity.

6. The method according to claim 1, wherein the composition comprises a crystalline complex of the SGLT2 inhibitor or pharmaceutically acceptable form thereof and an amino acid, and the amino acid is proline.

7. The method according to claim 1, wherein the SGLT2 inhibitor or pharmaceutically acceptable form thereof is administered orally or parenterally.

8. The method according to claim 1, wherein the SGLT2 inhibitor or pharmaceutically acceptable form thereof is administered orally.

9. The method according to claim 1, wherein the SGLT2 inhibitor or pharmaceutically acceptable form thereof is administered in a range of from 0.01 to 5 mg/kg body weight per day.

10. The method according to claim 1, wherein the SGLT2 inhibitor or pharmaceutically acceptable form thereof is administered in a range of from 0.02 to 1.0 mg/kg body weight per day.

11. The method according to claim 1, wherein the SGLT2 inhibitor or pharmaceutically acceptable form thereof is administered in a range of from 0.03 to 0.4 mg/kg body weight per day.

12. The method according to claim 1, wherein the SGLT2 inhibitor or pharmaceutically acceptable form thereof is administered once per day.

13. The method according to claim 1, wherein the equine animal is not obese and/or is present with muscle wasting and/or exhibits hyperglycemia.

14. The method of claim 1, wherein the composition comprises a 1:1:1 crystalline complex of the SGLT2 inhibitor or pharmaceutically acceptable form thereof, L-proline and water in a crystalline form.

15. The method according to claim 14, wherein the 1:1:1 crystalline complex is characterized by an X-ray powder diffraction pattern that comprises peaks at 20.28, 21.14 and 21.64 degrees 2Θ (±0.1 degrees 2Θ), wherein said X-ray powder diffraction pattern is made using $CuK_{\alpha 1}$ radiation.

16. The method of claim 1, wherein said laminitis, vascular dysfunction, hypertension, hepatic lipidosis, atherosclerosis, hyperadrenocorticism, Pituitary Pars Intermedia Dysfunction and/or Equine Metabolic Syndrome is associated with insulin resistance and/or hyperinsulinemia.

* * * * *